(12) United States Patent
Kojima

(10) Patent No.: US 10,786,193 B2
(45) Date of Patent: Sep. 29, 2020

(54) SYSTEM AND METHOD FOR ASSESSING AROUSAL LEVEL OF DRIVER OF VEHICLE THAT CAN SELECT MANUAL DRIVING MODE OR AUTOMATED DRIVING MODE

(71) Applicant: PANASONIC INTELLECTUAL PROPERTY MANAGEMENT CO., LTD., Osaka (JP)

(72) Inventor: Yoshihiro Kojima, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/661,574

(22) Filed: Oct. 23, 2019

(65) Prior Publication Data

US 2020/0054264 A1 Feb. 20, 2020

Related U.S. Application Data

(63) Continuation of application No. 16/259,409, filed on Jan. 28, 2019, now Pat. No. 10,485,468, which is a
(Continued)

(30) Foreign Application Priority Data

Feb. 8, 2017 (JP) ................. 2017-021599

(51) Int. Cl.
*G08B 23/00* (2006.01)
*A61B 5/18* (2006.01)
(Continued)

(52) U.S. Cl.
CPC .............. *A61B 5/18* (2013.01); *A61B 5/0077* (2013.01); *A61B 5/024* (2013.01); *A61B 5/11* (2013.01);
(Continued)

(58) Field of Classification Search
CPC ......... A61B 5/18; A61B 5/7246; A61B 5/024; A61B 5/6893; A61B 5/11; A61B 5/0077; A61B 5/7278; G08B 21/06; G08B 23/00
(Continued)

(56) References Cited

U.S. PATENT DOCUMENTS

2016/0041553 A1 2/2016 Sato et al.
2016/0090097 A1 3/2016 Grube et al.
(Continued)

FOREIGN PATENT DOCUMENTS

JP 06-171391 6/1994
JP 2014/181020 9/2014
(Continued)

*Primary Examiner* — Tanmay K Shah
(74) *Attorney, Agent, or Firm* — Greenblum & Bernstein, P.L.C.

(57) ABSTRACT

An apparatus assesses an arousal level of a driver of a vehicle. The apparatus includes a processor and a memory storing a computer program, which when executed by the processor, causes the processor to perform operations. The operations include acquiring personal data of the driver, which are detected by one or more sensors when the vehicle is traveling. The operations also include developing, by machine learning with the acquired personal data, a model for estimating an arousal level to personalize the model to the driver, and determining the arousal level of the driver based on the personalized model.

10 Claims, 8 Drawing Sheets

Related U.S. Application Data continuation of application No. 15/847,994, filed on Dec. 20, 2017, now Pat. No. 10,231,660.

(51) Int. Cl.
    *A61B 5/00*         (2006.01)
    *A61B 5/024*       (2006.01)
    *A61B 5/11*         (2006.01)
    *G08B 21/06*       (2006.01)

(52) U.S. Cl.
    CPC .......... *A61B 5/6893* (2013.01); *A61B 5/7246* (2013.01); *A61B 5/7278* (2013.01); *G08B 21/06* (2013.01); *G08B 23/00* (2013.01)

(58) Field of Classification Search
    USPC ........................................................ 340/576
    See application file for complete search history.

(56) References Cited

U.S. PATENT DOCUMENTS

| | | |
|---|---|---|
| 2016/0264131 A1 | 9/2016 | Chan et al. |
| 2017/0110022 A1 | 4/2017 | Gulash |
| 2018/0093675 A1 | 4/2018 | Holub et al. |
| 2018/0118219 A1 | 5/2018 | Hiei et al. |
| 2019/0213429 A1 * | 7/2019 | Sicconi .............. G06K 9/00597 |

FOREIGN PATENT DOCUMENTS

| | | |
|---|---|---|
| JP | 2015-219771 | 12/2015 |
| JP | 2016-038768 | 3/2016 |
| WO | 2014/148025 | 9/2014 |

* cited by examiner

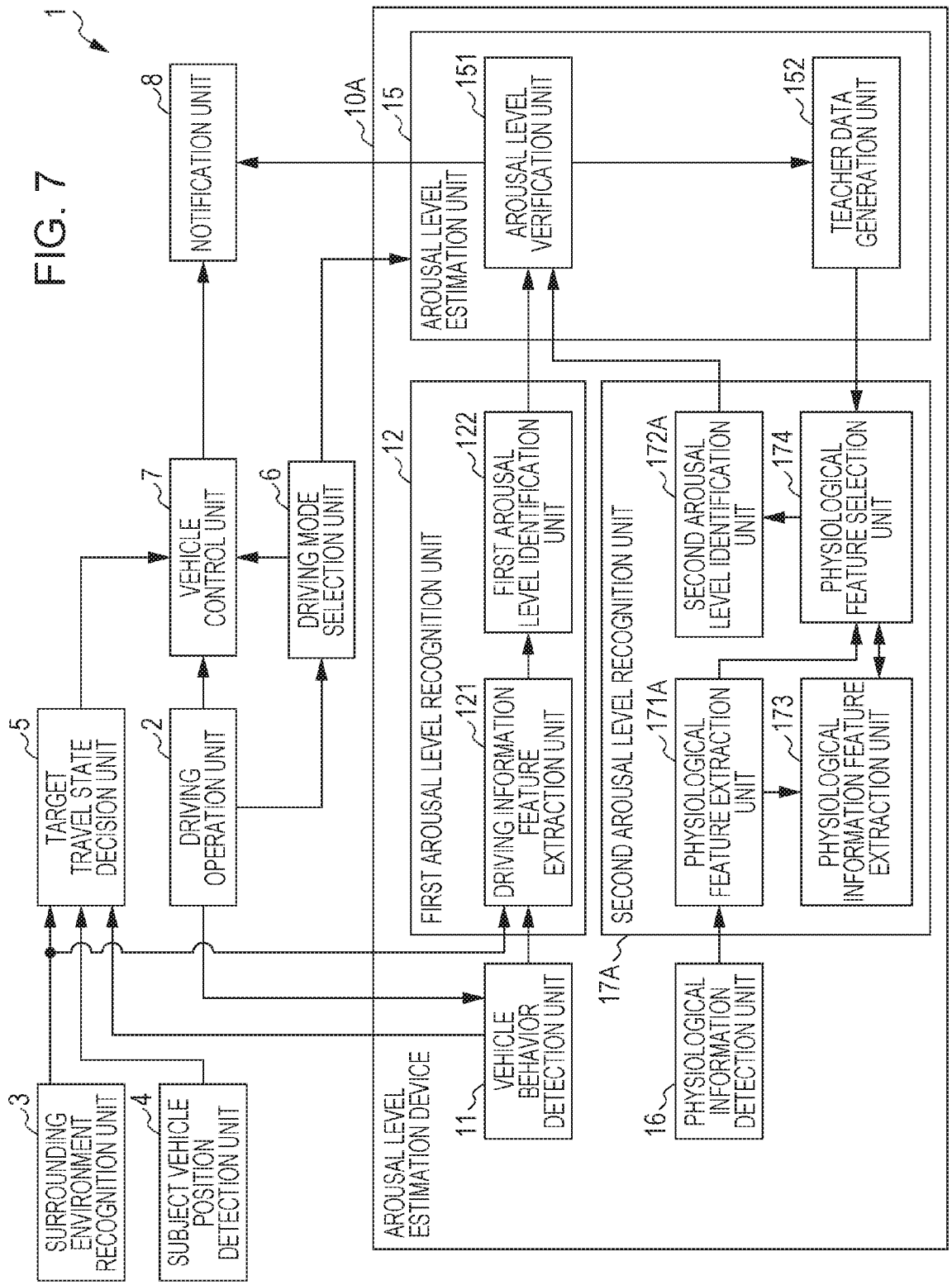

SYSTEM AND METHOD FOR ASSESSING AROUSAL LEVEL OF DRIVER OF VEHICLE THAT CAN SELECT MANUAL DRIVING MODE OR AUTOMATED DRIVING MODE

CROSS-REFERENCE TO RELATED APPLICATIONS

This application is a continuation of U.S. application Ser. No. 16/259,409, filed Jan. 28, 2019, which is a continuation of U.S. application Ser. No. 15/847,994, filed Dec. 20, 2017 and now U.S. patent Ser. No. 10/231,660 issued Mar. 19, 2019, which claims priority of Japanese Patent Application No. 2017-021599, filed Feb. 8, 2017. The disclosure of each of these documents, including the specification, drawings, and claims, is incorporated herein by reference in its entirety.

BACKGROUND

1. Technical Field

The present disclosure relates to an arousal level assessment system and an arousal level assessment method. The present disclosure relates particularly to an arousal level assessment system and an arousal level assessment method for assessing arousal level of a driver of a vehicle.

2. Description of the Related Art

In recent years, automated driving systems that automatically perform travel control of a vehicle such as acceleration, steering, and braking of the vehicle have been actively researched and developed.

For example, Japanese Unexamined Patent Application Publication No. 6-171391 discloses an arousal level estimation device that estimates the arousal level of a driver based on a driving operation which is detected by a driving operation detection sensor which monitors the driving operation by the driver in automated driving by using adaptive cruise control (ACC). Note that the arousal level indicates the scale that indicates the degree of awakening. For example, in a case where sleepiness occurs to the driver, the arousal level lowers.

The arousal level estimation device disclosed in Japanese Unexamined Patent Application Publication No. 6-171391 estimates the arousal level of the driver by using a fluctuation pattern in the steering angle that corresponds to the steering operation by the driver, assumes that the driver experiences sleepiness in a case where the arousal level of the driver is estimated to be low, actuates an alarm or the like, and thereby awakes the driver. Further, in a case where the frequency of alarm actuation becomes a prescribed frequency or more, the vehicle is decelerated by actuating a brake device of the vehicle or is further forcibly stopped. In such a manner, the arousal level estimation device disclosed in Japanese Unexamined Patent Application Publication No. 6-171391 may realize certain safe travel.

SUMMARY

In one general aspect, the techniques disclosed here feature a system for assessing arousal level of a driver of a vehicle, the system including at least one first sensor, at least one second sensor, and a processor. The processor (A) acquires driving mode information that indicates a driving mode of the vehicle, the driving mode being selectable by the vehicle and/or the driver from a first mode in which travel control of the vehicle is performed by the driver and a second mode in which at least a portion of the travel control of the vehicle is automatically performed, (B) assesses which of the first mode or the second mode is selected based on the driving mode information, (C) in a case where the first mode is selected, (c1) acquires driving information that indicates a driving operation by the driver and/or indicates a driving state of the vehicle via the at least one first sensor, (c2) acquires physiological information of the driver via the at least one second sensor, and (c3) assesses the arousal level based on the driving information and the physiological information, and (D) in a case where the second mode is selected, (d1) acquires the physiological information via the at least one second sensor, and (d2) assesses the arousal level based on the physiological information without referring to the driving information.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 is a block diagram that illustrates one example of a configuration of the driving support device in a modification example.

Figure 1:
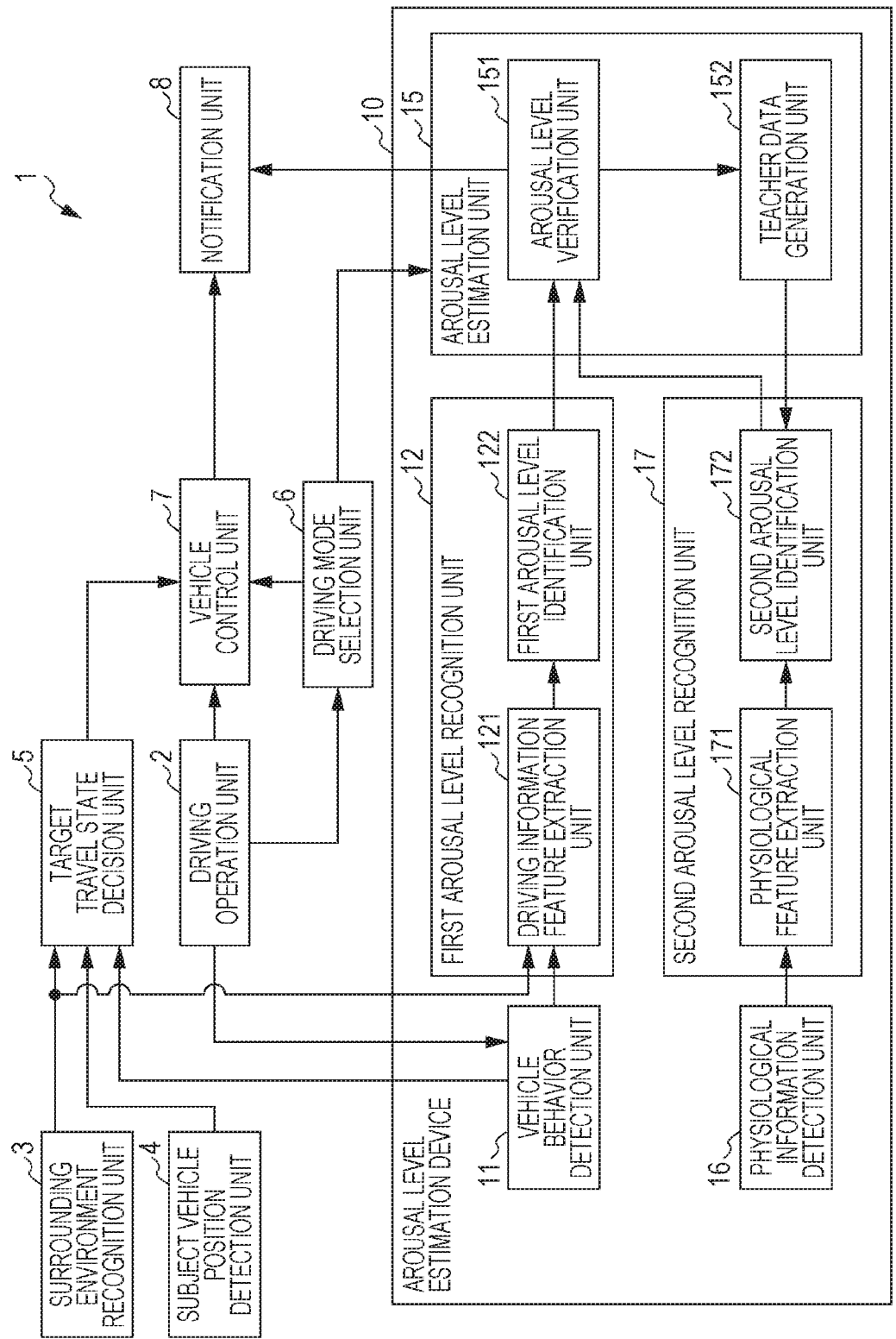
FIG. 1 is a block diagram that illustrates one example of a configuration of a driving support device in an embodiment.

DETAILED DESCRIPTION (Underlying Knowledge Forming Basis of Present Disclosure)

The underlying knowledge forming basis of the present disclosure will hereinafter be described.

As described above, in recent years, automated driving systems that automatically perform travel control of a vehicle such as acceleration, steering, and braking of the vehicle have been actively researched and developed. The automated driving system has automation levels, and widely-used automation levels are defined in view of division of roles related to driving between a driver and a system. For example, the automation levels that are defined by the National Highway Traffic Safety Administration of the U.S. Department of Transportation are categorized into five levels. Manual driving is categorized as level 0, and fully automated driving is categorized as level 4.

At the present time, the automation level of the automated driving systems that are installed in many vehicles is level 1. Level 1 is defined not as automated driving but as safe driving support. Level 1 indicates a state where adaptive cruise control (ACC), lane keeping assist (LKA), or the like is independently used for the vehicle. Accordingly, at level 1, the automated driving system performs vehicle control in either one of the front-rear direction or the left-right direction of the vehicle, and the driver performs the other vehicle control and monitoring of the traffic situation. Further, at level 1, the responsibility for safe driving is on the driver.

For example, the automated driving system of a vehicle that is equipped with the ACC automatically performs travel control that causes the vehicle to travel at a preset vehicle speed in a case where a preceding vehicle is not present and that adjusts the vehicle speed so as to maintain a preset vehicular gap in a case where a preceding vehicle is detected in the front. While the travel control is automatically performed by the automated driving system, because the driver does not have to perform pedal operations, the driving operations by the driver are only steering operations and are quite monotonous. Thus, the driver may become less mindful, and it is possible that the driver performs other work than driving or the arousal level lowers (sleepiness occurs). That is, it is possible that, although the driver is responsible for safe driving with the automated driving system of the vehicle equipped with the ACC, the driver excessively trusts the ACC and becomes careless about attention to and monitoring of a surrounding environment.

In such a manner, in a case where the automated driving system suddenly falls into a functional limit when the consciousness of the driver about driving lowers, it may be considered that the possibility that the response of the driver to a target object to which attention has to be paid in driving is delayed or the driver misses the target object becomes high. Further, in the worst case, this possibly results in a traffic accident.

Accordingly, in order to simultaneously satisfy comfort by use of the ACC and safe driving by the driver, a technique has been suggested which monitors the state of the driver, particularly, the arousal level and alerts the driver in a case where the arousal level becomes lower than an acceptable value when a function of the automated driving such as the ACC is used (For example, Japanese Unexamined Patent Application Publication No. 6-171391).

As described above, Japanese Unexamined Patent Application Publication No. 6-171391 discloses an arousal level estimation device that estimates the arousal level of a driver based on a driving operation which is detected by a driving operation detection sensor in automated driving by using the ACC. Specifically, the arousal level estimation device disclosed in Japanese Unexamined Patent Application Publication No. 6-171391 monitors a fluctuation pattern in the steering angle of the steering by the driver and estimates the arousal level of the driver based on a frequency feature of the pattern. In a case where the arousal level of the driver is estimated to be low, an alarm or the like is actuated, and the driver is thereby awoken. Further, in a case where the frequency of alarm actuation becomes a prescribed frequency or more, the vehicle is decelerated by actuating a brake device or is further forcibly stopped. In such a manner, the arousal level estimation device disclosed in Japanese Unexamined Patent Application Publication No. 6-171391 may realize certain safe travel.

At the present time, as a next generation automated driving system, automated driving systems whose automation level is level 2 are being partially put to practical use. Because the automated driving system at level 2 performs the vehicle control in the front-rear direction and the left-right direction of the vehicle by fully using of the ACC, the LKA, and so forth, the driver does not have to perform pedal operations or steering operations. However, because the responsibility for safe driving at level 2 is on the driver similarly to level 1, the driver has to regularly monitor the automated driving system and the surrounding environment in case of the functional limit of the automated driving system.

However, at level 2, because the driver has to perform few driving operations as long as the automated driving system stably acts, the possibility that the consciousness about driving or arousal level lowers becomes higher than level 1. For example, in a case where the automated driving system falls into the functional limit or fails, the driver has to take over the driving operation from the automated driving system. However, in a case where switching is made to manual driving when the arousal level of the driver lowers, it is possible that the response of the driver to a target object to which attention has to be paid in driving of the vehicle is delayed or the driver misses the target object, and this further results in a traffic accident in the worst case.

Accordingly, in order to realize the automated driving system at level 2 or higher, the state of the driver in the automated driving, particularly, the arousal level is monitored, the driver is alerted in a case where the arousal level becomes lower than the acceptable value, and the accident due to lowering in the arousal level has to be thereby prevented. Particularly, a method for precisely estimating the arousal level of the driver in the automated driving is an important problem.

Meanwhile, in the arousal level estimation device disclosed in Japanese Unexamined Patent Application Publication No. 6-171391, as described above, a method is disclosed which estimates the arousal level of the driver based on the driving operation by the driver in the automated driving at level 1 by using the ACC, that is, based on the fluctuation pattern in the steering angle which corresponds to the steering operation by the driver. Usually, in a case where the arousal level lowers, the driver may not accurately perform the steering operation and frequently performs rapid correction of the steering angle. Accordingly, the rapid correction of the steering angle in the steering operation by the driver may be detected by using a frequency feature of the fluctuation pattern in the steering angle in a unit time. Thus, based on the detection result, the arousal level of the driver may be estimated.

However, as described above, there is a problem in that the arousal level estimation device disclosed in Japanese Unexamined Patent Application Publication No. 6-171391 may not estimate the arousal level for the automated driving system at level 2 or higher in which the driver performs few driving operations such as the steering operation.

Meanwhile, for example, Japanese Unexamined Patent Application Publication No. 2014-181020 or Japanese Unexamined Patent Application Publication No. 2016-38768 discloses a method for estimating the arousal level of the driver by using physiological information of the driver that is other information than the driving operation. More specifically, Japanese Unexamined Patent Application Publication No. 2014-181020 discloses a method in which the state of the driver such as an eye opening ratio that is an opening magnitude of an eye of the driver, for example, is detected from a face image of the driver in the automated driving, which is acquired by using an in-vehicle camera, and the arousal level of the driver is thereby estimated. Japanese Unexamined Patent Application Publication No. 2016-38768 discloses a method in which the arousal level of the driver is estimated based on the physiological information of the driver in the automated driving such as heart rate information or brain wave information, for example, which is detected by using a wearable physiological sensor. Using the method disclosed in Japanese Unexamined Patent Application Publication No. 2014-181020 or Japanese Unexamined Patent Application Publication No. 2016-38768 enables the arousal level of the driver to be estimated without using the driving operation by the driver. That is, it is possible to estimate the arousal level of the driver even for the automated driving system at level 2 or higher in which the driver performs few driving operations.

However, there is a problem in that sufficient precision may not be obtained because in general the physiological information widely varies due to individual differences. For example, in the method disclosed in Japanese Unexamined Patent Application Publication No. 2014-181020, the sleepiness of the driver is estimated to become higher, that is, the arousal level is estimated to become lower as the eye opening ratio, which is the opening magnitude of the eye of the driver, becomes lower. However, because the driver who habitually opens his/her eye widely and the driver who does not are present, the arousal level of all the drivers may not be estimated precisely based on the eye opening ratio that uses the same reference. Similarly, in the method disclosed in Japanese Unexamined Patent Application Publication No. 2016-38768, the arousal level is estimated by using the heart rate information or the brain waves of the driver. However, the precision of those pieces of physiological information related to the autonomic nervous system and the central nervous system more widely varies due to individual differences than the eye opening ratio. Accordingly, in order to precisely estimate the arousal level by using the physiological information of the driver, an estimation method that absorbs variations of the physiological information due to individual differences is requested.

Regarding the request, as a method that absorbs variations due to individual differences among the drivers, a method has been contrived which causes an arousal level estimation model for estimating the arousal level to have a learning function and thereby generates the arousal level estimation model of an individual driver. Specifically, a method has been contrived in which model learning is successively performed for the arousal level estimation model common to the drivers by using teacher data of the individual driver and thereby the arousal level estimation model for the individual driver is finally generated.

However, there is a problem in that how the teacher data of the individual driver are generated for the driver in driving may not be known. At the present time, as the teacher data for the arousal level estimation model, for example, a subjective evaluation value that is reported by the driver himself/herself or a facial expression evaluation value that is obtained from subjective estimation of a facial expression video of the driver by a third party is most frequently used. However, it is very difficult to acquire such data in real time from the driver in driving.

Incidentally, at the present time, it is considered to be technically very difficult for the vehicle to regularly travel in usual urban areas in an automated driving mode at level 2 or higher after the driver rides on the vehicle and starts driving and until the vehicle arrives at a destination and the driver finishes driving. This is because the automated driving system has to completely recognize the traffic situation around the vehicle but infrastructure construction for complete recognition of the traffic situation around the vehicle is not realized. Thus, for the time being, it is considered that the travel control of the vehicle is performed by using a manual driving mode at level 0 or a safe driving support mode at level 1 in the urban areas and by using the automated driving mode at level 2 or higher in suburban areas and on highways. That is, for the time being, it is considered that the driver performs driving by appropriately switching the manual driving mode and the automated driving mode in accordance with the surrounding environment.

Accordingly, as a result of intensive studies, the inventor has found that in manual driving, the arousal level estimation model that uses the physiological information of the driver learns estimation results of the arousal level estimation model, which uses driving information such as the driving operations by the driver or vehicle behavior, as the teacher data and the variations in the arousal level estimation model that uses the physiological information due to individual differences may thereby be absorbed.

An arousal level estimation device according to one aspect of the present disclosure is an arousal level estimation device that estimates arousal level of a driver of a vehicle, the vehicle being capable of switching an automated driving mode in which travel control of the vehicle is automatically performed and a manual driving mode in which the travel control of the vehicle is performed by the driver. The arousal level estimation device includes a vehicle behavior detection unit that detects driving information of the vehicle, a first arousal level recognition unit that recognizes first arousal level of the driver from the driving information detected by the vehicle behavior detection unit, a physiological information detection unit that detects one or more pieces of physiological information of the driver, a second arousal level recognition unit that recognizes second arousal level of the driver from the one or more pieces of physiological information detected by the physiological information detection unit, and an arousal level estimation unit that estimates third arousal level of the driver in traveling of the vehicle from at least one of the first arousal level recognized by the first arousal level recognition unit and the second arousal level recognized by the second arousal level recognition unit. The arousal level estimation unit estimates the third arousal level from the first arousal level and the second arousal level in the manual driving mode and estimates the third arousal level from the second arousal level in the automated driving mode.

Consequently, the recognition units each of which recognizes the arousal level of the driver may selectively be used in the manual driving mode and the automated driving mode. Thus, the arousal level of the driver of the vehicle that has the automated driving mode and the manual driving mode may be estimated highly precisely.

Further, in the automated driving mode, the arousal level estimation unit may set the second arousal level as the third arousal level and may thereby estimate the third arousal level from the second arousal level.

Further, in the manual driving mode, the arousal level estimation unit may assess whether or not reliability of each of the first arousal level and the second arousal level is equal to or higher than a threshold value, set one of the first arousal level and the second arousal level, whose reliability is equal to or higher than the threshold value, as the third arousal level, and thereby estimate the third arousal level.

Further, in the manual driving mode, in a case where the reliability of each of the first arousal level and the second arousal level is equal to or higher than the threshold value and the first arousal level is different from the second arousal level, the arousal level estimation unit may set the first arousal level as the third arousal level and thereby estimate the third arousal level.

Further, in the manual driving mode, in a case where the first arousal level is different from the second arousal level, the arousal level estimation unit may cause the second arousal level recognition unit to perform a learning process such that the second arousal level recognition unit outputs the first arousal level as a recognition result by using teacher data that are generated based on the first arousal level.

Consequently, in the manual driving mode, an estimation model of the second arousal level is learned by using the teacher data generated from the first arousal level, and variations in precision due to individual differences in the physiological information may thereby be absorbed. Accordingly, it is possible to precisely estimate the arousal level of the driver even in the automated driving system at level 2 or higher in which the driving information of the driver may not be used.

Further, in the learning process, an arousal level identification model for recognizing the second arousal level, which indicates the relationship between one or more pieces of physiological information of the driver and the arousal level of the driver, may be updated such that the arousal level identification model for recognizing the second arousal level outputs the first arousal level as an identification result.

Further, the second arousal level recognition unit may include a physiological feature extraction unit that extracts a physiological information feature related to a physiological state of the driver from each of plural pieces of physiological information detected by the physiological information detection unit and a physiological feature selection unit that selects the physiological information feature, which is highly correlated with the teacher data generated from the first arousal level, among plural physiological information features extracted by the physiological feature extraction unit, and the arousal level estimation unit may cause the second arousal level recognition unit to perform the learning process such that the second arousal level recognition unit outputs the first arousal level as a recognition result by using the physiological information feature that is selected by the physiological feature selection unit as the teacher data.

Further, the physiological information may be information that indicates a heart rate fluctuation of the driver.

Further, the physiological information may be a face image in which a face of the driver appears.

Further, the physiological information may be information that indicates body movement of the driver.

Further, the driving information may be information that indicates a steering angle of the vehicle.

Further, the driving information may be information that indicates positions of an accelerator pedal and a brake pedal of the vehicle.

Further, the driving information may be information that indicates acceleration of the vehicle.

Further, an arousal level estimation method according to one aspect of the present disclosure is an arousal level estimation method for estimating arousal level of a driver of a vehicle, the vehicle being capable of switching an automated driving mode in which travel control of the vehicle is automatically performed and a manual driving mode in which the travel control of the vehicle is performed by the driver. The arousal level estimation method includes a vehicle behavior detection step of detecting driving information of the vehicle, a first arousal level recognition step of recognizing first arousal level of the driver from the driving information detected in the vehicle behavior detection step, a physiological information detection step of detecting physiological information of the driver, a second arousal level recognition step of recognizing second arousal level of the driver from the physiological information detected in the physiological information detection step, and an arousal level estimation step of estimating third arousal level of the driver in traveling of the vehicle from at least one of the first arousal level recognized in the first arousal level recognition step and the second arousal level recognized in the second arousal level recognition step. In the arousal level estimation step, the third arousal level is estimated based on the first arousal level and the second arousal level in the manual driving mode, and the third arousal level is estimated based on the second arousal level in the automated driving mode.

Note that the present disclosure may be realized not only as a device but also realized as an integrated circuit that includes a processing section which is included in such a device, a method including steps using the processing section which configures the device, a program that causes a computer to execute the steps, and information, data, or signals that indicate the program. Further, the program, information, data, and signals may be delivered via a recording medium such as a CD-ROM or a communication medium such as the Internet.

Embodiments of the present disclosure will hereinafter be described with reference to drawings.

Note that all the embodiments described below illustrate general or specific examples. Values, shapes, materials, configuration elements, arrangement positions or connection manners of configuration elements, steps, orders of steps, and so forth that are described in the following embodiments are examples and are not intended to limit the present disclosure. Further, the configuration elements that are not described in the independent claims which provide the most superordinate concepts among the configuration elements in the following embodiments will be described as arbitrary configuration elements.

Embodiment

A driving support device according to an embodiment will hereinafter be described.

[1. Configuration of Driving Support Device 1]

FIG. 1 is a block diagram that illustrates one example of a configuration of a driving support device 1 in this embodiment.

The driving support device 1 is a device that is installed in a vehicle, estimates the arousal level of a driver in driving, alerts the driver in a case where the estimated arousal level is lower than a prescribed value, and thereby inhibits drowsy driving by the driver. In this embodiment, a description will be made in the following on an assumption that the vehicle is capable of switching an automated driving mode in which travel control of the vehicle is automatically performed and a manual driving mode in which the travel control of the vehicle is performed by a driving operation by the driver.

As illustrated in FIG. 1, the driving support device 1 includes a driving operation unit 2, a surrounding environment recognition unit 3, a subject vehicle position detection unit 4, a target travel state decision unit 5, a driving mode selection unit 6, a vehicle control unit 7, a notification unit 8, and an arousal level estimation device 10.

<Driving Operation Unit 2>

Figure 2A:
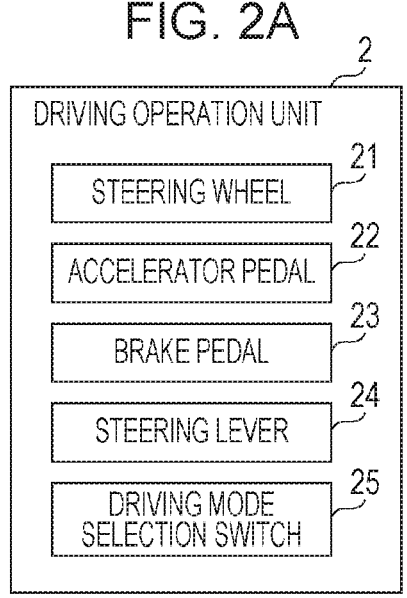
FIG. 2A is a block diagram that illustrates one example of a specific configuration of a driving operation unit illustrated in FIG. 1.

FIG. 2A is a block diagram that illustrates one example of a specific configuration of the driving operation unit 2 illustrated in FIG. 1.

The driving operation unit 2 is operated in order for the driver to drive the vehicle. For example, as illustrated in FIG. 2A, the driving operation unit 2 includes a steering wheel 21, an accelerator pedal 22, a brake pedal 23, a steering lever 24 such as a shift lever, and a driving mode selection switch 25 for selecting a driving mode. Note that the pedals included in the driving operation unit 2 are not limited to the accelerator pedal 22 and the brake pedal 23. Further, the driving operation unit 2 may include other components than the above.

<Surrounding Environment Recognition Unit 3>

Figure 2B:
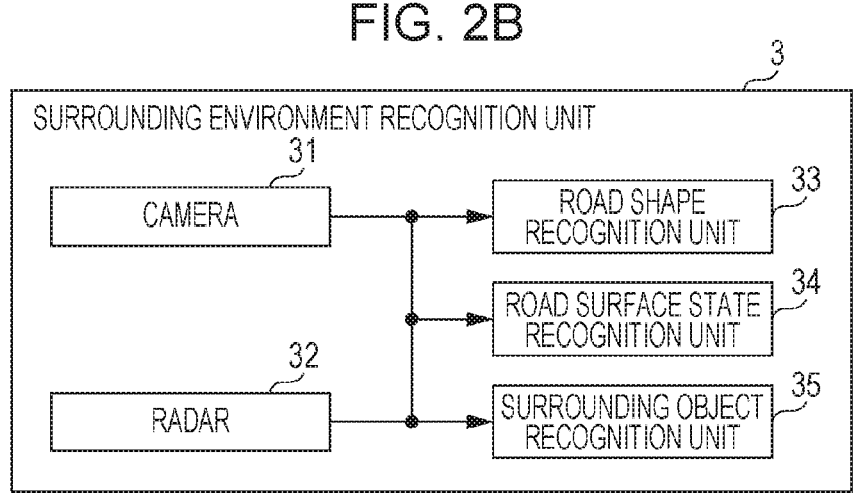
FIG. 2B is a block diagram that illustrates one example of a specific configuration of a surrounding environment recognition unit illustrated in FIG. 1.

FIG. 2B is a block diagram that illustrates one example of a specific configuration of the surrounding environment recognition unit 3 illustrated in FIG. 1.

The surrounding environment recognition unit 3 includes plural sensors and plural recognition units and recognizes a surrounding environment of the subject vehicle.

The plural sensors detect various kinds of information for monitoring an outside situation of the subject vehicle. For example, as illustrated in FIG. 2B, the plural sensors include a camera 31 and a radar 32. At least one or more cameras 31 are arranged on an external surface of the vehicle, for example, and image an outside environment of the vehicle such as a lane, a road surface, and a surrounding obstacle. The radar 32 is a millimeter-wave radar or a laser radar that is arranged in a front portion or a rear portion of the vehicle, for example, and measures the distances to and the positions of a vehicle or an obstacle that is present around the subject vehicle, and so forth.

The plural recognition units recognize the surrounding environment of the subject vehicle based on the information detected from each of the sensors. For example, as illustrated in FIG. 2B, the plural recognition units include a road shape recognition unit 33, a road surface state recognition unit 34, and a surrounding object recognition unit 35. The road shape recognition unit 33 recognizes a road shape around the subject vehicle. The road shape recognition unit 33 recognizes the lane such as a white line on a road from a photographed image by the camera 31 and detects the width, the curvature, and so forth of the lane. The road surface state recognition unit 34 recognizes a road surface state in front of the subject vehicle. The road surface state recognition unit 34 recognizes the road surface state such as a snow accumulation or black ice from a photographed image by the camera 31. The surrounding object recognition unit 35 recognizes an object that is present around the subject vehicle. The surrounding object recognition unit 35 recognizes a pedestrian, a bicycle, a motorcycle, or another surrounding vehicle by using photographed images by the camera 31 and radar information by the radar 32 and detects the size, position, speed, movement direction, or the like of the recognized object.

<Subject Vehicle Position Detection Unit 4>

Figure 2C:
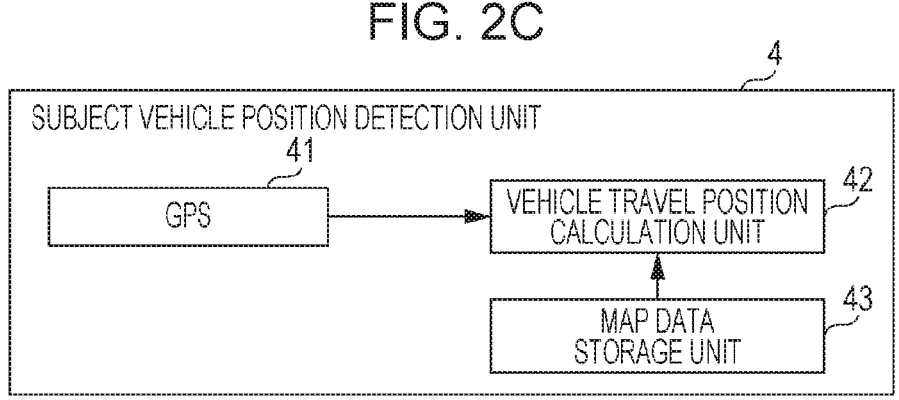
FIG. 2C is a block diagram that illustrates one example of a specific configuration of a subject vehicle position detection unit illustrated in FIG. 1.

FIG. 2C is a block diagram that illustrates one example of a specific configuration of the subject vehicle position detection unit 4 illustrated in FIG. 1.

As illustrated in FIG. 2C, the subject vehicle position detection unit 4 includes a global positioning system (GPS) 41, a vehicle travel position calculation unit 42, and a map data storage unit 43 and detects the position of the subject vehicle on the map. The GPS 41 receives GPS information that indicates the position of the subject vehicle from GPS satellites. The map data storage unit 43 in advance stores map data. The vehicle travel position calculation unit 42 calculates the travel position of the subject vehicle on the map data that are stored in the map data storage unit 43 based on the received GPS information.

<Target Travel State Decision Unit 5>

The target travel state decision unit 5 decides a target travel state that is a travel state of the subject vehicle to be a target. In the example illustrated in FIG. 1, the target travel state decision unit 5 calculates information of the target travel state based on present surrounding environment information that is obtained from the surrounding environment recognition unit 3, a present subject vehicle position that is obtained from the subject vehicle position detection unit 4, and present subject vehicle behavior that is obtained from a vehicle behavior detection unit 11. Note that information of the travel state includes information related to travel of the vehicle such as the position of the vehicle or the speed or orientation of the vehicle in the position. The target travel state may be calculated by a method in related art, and a description thereof will thus not be made here.

<Driving Mode Selection Unit 6>

The driving mode selection unit 6 switches the driving mode of the vehicle to either one of the automated driving mode and the manual driving mode. In the example illustrated in FIG. 1, the driving mode selection unit 6 switches the driving mode to either one of the automated driving mode and the manual driving mode in accordance with the operation of the driving mode selection switch 25 of the driving operation unit 2 by the driver.

<Vehicle Control Unit 7>

The vehicle control unit 7 is configured with a CPU or the like that realizes a prescribed function in cooperation with software, for example, and performs the travel control of the vehicle based on the presently-selected driving mode. For example, in the automated driving mode, the vehicle control unit 7 controls various actuators for acceleration, steering, and braking of the subject vehicle, an ECU, and so forth based on the target travel state that is obtained from the target travel state decision unit 5. Further, for example, in the manual driving mode, the vehicle control unit 7 controls the various actuators for acceleration, steering, and braking of the subject vehicle, the ECU, and so forth in accordance with the operation of the driving operation unit 2 by the driver.

<Notification Unit 8>

The notification unit 8 is configured with various in-vehicle displays such as a car navigation system, a speaker, a driver seat that has a vibration actuator built therein, or the like, for example. The notification unit 8 provides notification of the driving mode that is selected by the driver or information that indicates the present vehicle position. Further, the notification unit 8 notifies the driver of predetermined information in accordance with the arousal level that is estimated by an arousal level estimation unit 15. For example, the notification unit 8 provides notification of an alert or a warning that suppresses the sleepiness of the driver in a case where a determination is made that the arousal level of the driver becomes lower than a prescribed value, that is, the sleepiness equal to or higher than a prescribed value occurs to the driver.

<Arousal Level Estimation Device 10>

The arousal level estimation device 10 is one example of an arousal level estimation device in the present disclosure and estimates the arousal level of the driver in driving of the vehicle. A specific configuration and so forth of the arousal level estimation device 10 will hereinafter be described with reference to the drawings.

[Configuration of Arousal level Estimation Device 10]

Figure 3:
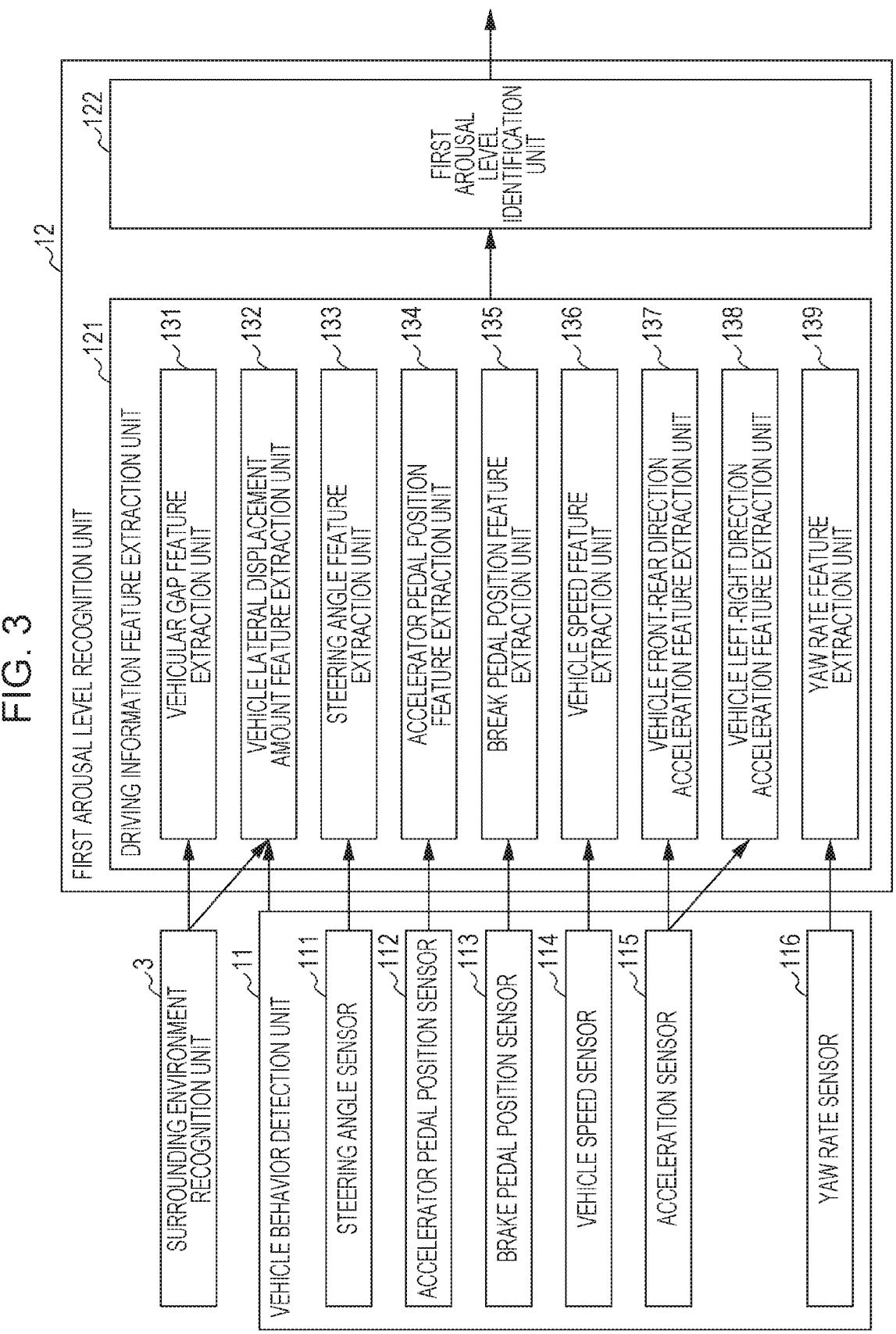
FIG. 3 is a block diagram that illustrates examples of specific configurations of a vehicle behavior detection unit and a first arousal level recognition unit, which are illustrated in FIG. 1.
Figure 4:
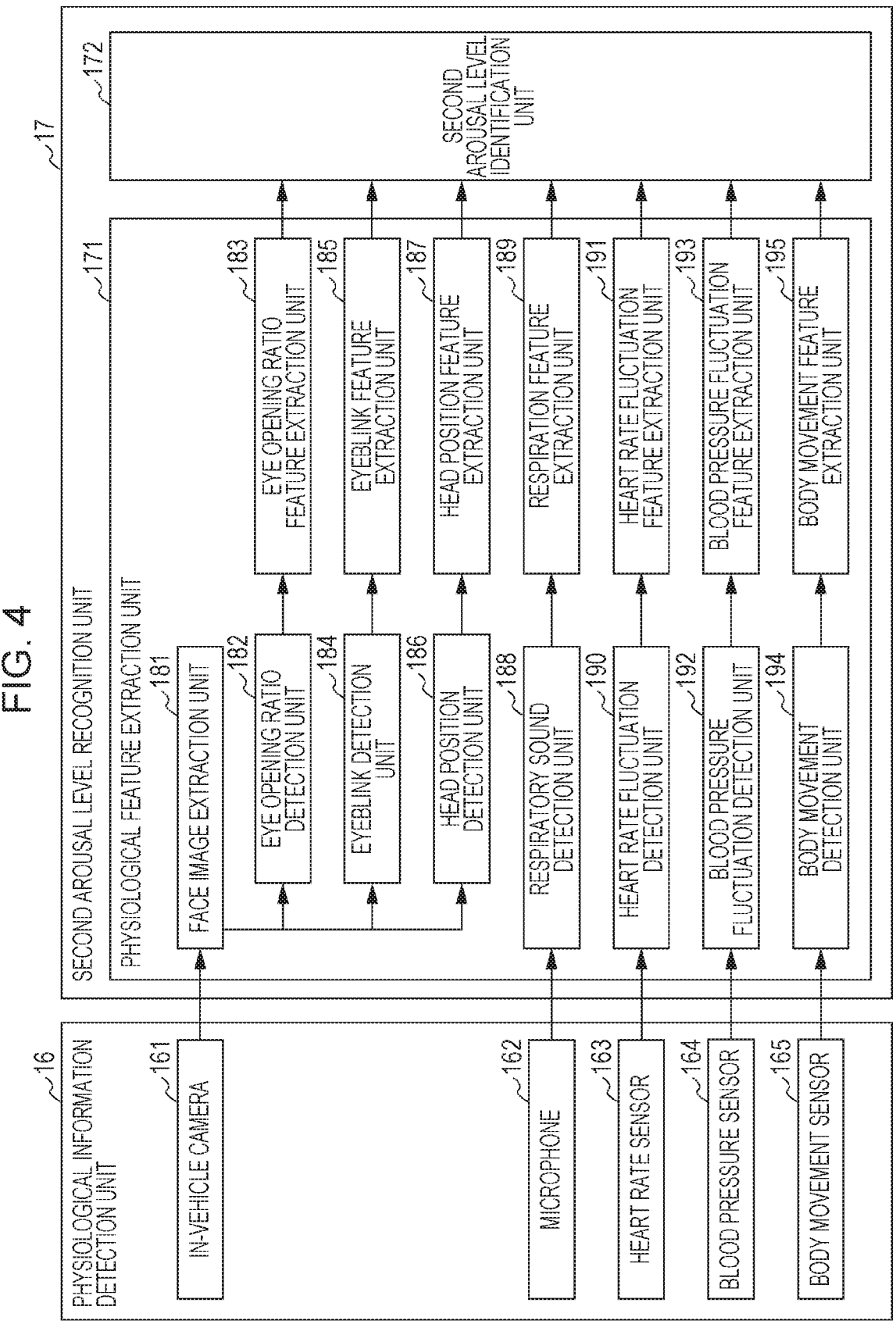
FIG. 4 is a block diagram that illustrates examples of specific configurations of a physiological information detection unit and a second arousal level recognition unit, which are illustrated in FIG. 1.

FIG. 3 is a block diagram that illustrates examples of specific configurations of the vehicle behavior detection unit 11 and a first arousal level recognition unit 12, which are illustrated in FIG. 1. FIG. 4 is a block diagram that illustrates examples of specific configurations of a physiological information detection unit 16 and a second arousal level recognition unit 17, which are illustrated in FIG. 1.

As illustrated in FIG. 1, the arousal level estimation device 10 includes the vehicle behavior detection unit 11, the first arousal level recognition unit 12, the arousal level estimation unit 15, the physiological information detection unit 16, and the second arousal level recognition unit 17. Note that the arousal level (sleepiness) of the driver that is estimated by the arousal level estimation device 10 is decided as any one of five levels of level 1 to level 5, for example. For example, level 1 indicates "not sleepy state", and level 2 indicates "slightly sleepy state". Level 3 indicates "sleepy state", and level 4 indicates "fairly sleepy state". Level 5 indicates "very sleepy state".

<Vehicle Behavior Detection Unit 11>

The vehicle behavior detection unit 11 detects driving information. In this embodiment, the vehicle behavior detection unit 11 is configured with a sensor group for detecting the driving information that indicates the driving operation by the driver and the behavior of the vehicle. This sensor group includes a sensor that detects the driving operation by the driver and a sensor that detects the behavior of the vehicle.

For example, as illustrated in FIG. 3, the sensor that detects the driving operation by the driver includes a steering angle sensor 111, an accelerator pedal position sensor 112, and a brake pedal position sensor 113. The steering angle sensor 111 detects the rotational angle of the steering wheel 21 in the driving operation unit 2, that is, the steering angle. The accelerator pedal position sensor 112 detects the position of the accelerator pedal 22 or the brake pedal 23. The brake pedal position sensor 113 detects the position of the brake pedal 23.

Further, the sensor that detects the behavior of the vehicle includes a vehicle speed sensor 114, an acceleration sensor 115, and a yaw rate sensor 116. The vehicle speed sensor 114 detects the speed of the vehicle. The acceleration sensor 115 detects the acceleration in the front-rear direction of the vehicle and the acceleration in the left-right direction of the vehicle. The yaw rate sensor 116 detects the rotational angle (yaw rate) with respect to the perpendicular direction of the vehicle.

<First Arousal Level Recognition Unit 12>

The first arousal level recognition unit 12 recognizes first arousal level of the driver from the driving information that is detected by the vehicle behavior detection unit 11. Here, for example, the driving information may be information that indicates the steering angle of the vehicle, may be information that indicates the positions of the accelerator pedal 22 and the brake pedal 23 of the vehicle, or may be information that indicates the acceleration of the vehicle. Here, for example, the driving information may be information that indicates the speed of the vehicle or may be information that indicates the yaw rate. In this embodiment, as illustrated in FIG. 3, the first arousal level recognition unit 12 includes a driving information feature extraction unit 121 and a first arousal level identification unit 122 and recognizes the first arousal level of the driver by using the surrounding environment of the subject vehicle that is recognized by the surrounding environment recognition unit 3 and the driving information that is detected by the vehicle behavior detection unit 11.

<<Driving Information Feature Extraction Unit 121>>

The driving information feature extraction unit 121 extracts a driving information feature from the surrounding environment of the subject vehicle that is recognized by the surrounding environment recognition unit 3 and the driving information that is detected by the vehicle behavior detection unit 11.

Here, the surrounding environment of the subject vehicle is information that indicates the vehicular gap between a preceding vehicle and the subject vehicle or the distance between the subject vehicle and the lane such as the white line of the road, for example. Further, as described above, the driving information is information that is detected by the sensor group included in the vehicle behavior detection unit 11 and that indicates the driving operation by the driver such as the steering angle of the steering wheel 21 or the behavior of the subject vehicle such as the speed of the vehicle, for example. Further, the driving information feature is a feature for identifying the first arousal level of the driver, the feature being related to a driving activity of the driver. Specifically, for example, the driving information features are statistical features such as average values and standard deviations that are obtained from fluctuation patterns in the steering angle of the steering wheel 21 which is operated by the driver and in the positions of the accelerator pedal 22 and the brake pedal 23 and fluctuation patterns in the vehicular gap from the preceding vehicle, the lateral displacement amount of the vehicle, the vehicle speed, the accelerations of the vehicle in the front-rear and left-right directions, the yaw rate, and so forth, in a prescribed unit time such as one minute.

In this embodiment, the driving information feature extraction unit 121 includes one or more feature extraction units and extracts at least one or more features that are related to the driving activity of the driver as the driving information features. For example, in the example illustrated in FIG. 3, the driving information feature extraction unit 121 has a vehicular gap feature extraction unit 131, a vehicle lateral displacement amount feature extraction unit 132, a steering angle feature extraction unit 133, an accelerator pedal position feature extraction unit 134, a brake pedal position feature extraction unit 135, a vehicle speed feature extraction unit 136, a vehicle front-rear direction acceleration feature extraction unit 137, a vehicle left-right direction acceleration feature extraction unit 138, and a yaw rate feature extraction unit 139.

The vehicular gap feature extraction unit 131 extracts a vehicular gap feature, which is the average value, standard deviation, or the like of the vehicular gap in a prescribed unit time, as the driving information feature by using the vehicular gap between the preceding vehicle and the subject vehicle that is obtained from the surrounding environment recognition unit 3.

The vehicle lateral displacement amount feature extraction unit 132 acquires, from the surrounding environment recognition unit 3, information of the road shape such as the width, the curvature, or the like of the lane and information that indicates the distance between the vehicle and the lane such as the distance from the white line of the road. The vehicle lateral displacement amount feature extraction unit 132 calculates the displacement amount of the vehicle from a center line of the road (hereinafter referred to as vehicle lateral displacement amount) based on the information of the road shape and the distance that is obtained from the surrounding environment recognition unit 3. Then, the vehicle lateral displacement amount feature extraction unit 132 extracts a vehicle lateral displacement feature, which is the average value, standard deviation, or the like of the vehicle lateral displacement amount in a prescribed unit time which is calculated by using the pieces of information and the displacement amount, as the driving information feature. Note that the vehicle lateral displacement amount may not be a simple displacement amount from the center line but may be the displacement amount from the travel position that is set as a target at the time after a prescribed unit time by the driver. Further, for example, as disclosed in Japanese Unexamined Patent Application Publication No. 2015-219771, a target travel position of the driver may be calculated based on the steering angle of the steering wheel 21, the speed of the vehicle, or the yaw rate, which is obtained from the vehicle behavior detection unit 11.

The steering angle feature extraction unit 133 extracts a steering angle feature, which is the average value or standard deviation of the displacement amount of the steering angle in a prescribed unit time, as the driving information feature by using the steering angle of the steering wheel 21 that is obtained from the steering angle sensor 111. Note that the steering angle feature extraction unit 133 may extract the steering angle feature, which is a frequency feature or the like of the displacement amount of the steering angle, as the driving information feature.

The accelerator pedal position feature extraction unit 134 extracts an accelerator pedal position feature, which is the average value, standard deviation, or the like of the displacement amount of the position of the accelerator pedal in a prescribed unit time, as the driving information feature by using the position of the accelerator pedal 22 that is obtained from the accelerator pedal position sensor 112.

The brake pedal position feature extraction unit 135 extracts a brake pedal position feature, which is calculated by using the position of the brake pedal 23 which is obtained from the brake pedal position sensor 113, as the driving information feature. Here, the brake pedal position feature is the average value or standard deviation of the displacement amount of the position of the brake pedal in a prescribed unit time, the frequency of brake operations, or the like.

The vehicle speed feature extraction unit 136 extracts a vehicle speed feature, which is the average value, standard deviation, or the like of the displacement amount of the vehicle speed in a prescribed unit time, as the driving information feature by using the vehicle speed that is obtained from the vehicle speed sensor 114.

The vehicle front-rear direction acceleration feature extraction unit 137 calculates the acceleration of the vehicle in the front-rear direction of the vehicle accelerations that are obtained from the acceleration sensor 115. Further, the vehicle front-rear direction acceleration feature extraction unit 137 extracts a vehicle front-rear direction acceleration feature, which is the average value, standard deviation, or the like of the displacement amount of the acceleration of the vehicle in the front-rear direction in a prescribed unit time, as the driving information feature by using the calculated acceleration of the vehicle in the front-rear direction.

The vehicle left-right direction acceleration feature extraction unit 138 calculates the acceleration of the vehicle in the left-right direction of the vehicle accelerations that are obtained from the acceleration sensor 115. Further, the vehicle left-right direction acceleration feature extraction unit 138 extracts a vehicle left-right direction acceleration feature, which is the average value, standard deviation, or the like of the displacement amount of the acceleration of the vehicle in the left-right direction in a prescribed unit time, as the driving information feature by using the calculated acceleration of the vehicle in the left-right direction.

The yaw rate feature extraction unit 139 extracts a yaw rate feature, which is the average value, standard deviation, or the like of the displacement amount of the yaw rate in a prescribed unit time, as the driving information feature by using the yaw rate that is obtained from the yaw rate sensor 116.

<<First Arousal Level Identification Unit 122>>

The first arousal level identification unit 122 identifies the first arousal level of the driver by using the driving information features that are extracted by the driving information feature extraction unit 121.

In this embodiment, the first arousal level identification unit 122 identifies the arousal level of the driver by using at least one or more features that are obtained from one or more feature extraction units of the driving information feature extraction unit 121 and outputs identification results as the first arousal level. The identification results include the arousal level that indicates any of level 1 to level 5 and the reliability of the arousal level, for example.

Here, a specific description will be made about an identification method of the first arousal level that is performed by the first arousal level identification unit 122.

It has been known that the driving operation of the vehicle by the driver becomes monotonous in a case where the arousal level of the driver lowers (the sleepiness becomes high) in driving. For example, the operations of the steering wheel 21, the accelerator pedal 22, or the brake pedal 23 by the driver lessen in a case where the sleepiness becomes high compared to a time before the sleepiness becomes high. Further, in a case where the sleepiness of the driver becomes high, the vehicle in driving wobbles, and the fluctuation in the lateral displacement amount of the vehicle, the vehicular gap, or the like tends to become large. For example, in a case where the sleepiness of the driver temporarily becomes high, a case occurs where the operations of the steering wheel 21 decrease and the vehicle wobbles hard. However, in a moment when the vehicle wobbles hard, the driver often awakes temporarily and takes an activity to rapidly operate the steering wheel 21 in order to correct the travel state of the vehicle to a right travel state. Further, in such a case, the fluctuation pattern in the displacement amount of the steering angle of the steering wheel 21 or the lateral displacement amount of the vehicle exhibit a feature pattern in which the displacement amount becomes comparatively small for a certain time and the displacement amount thereafter rapidly and largely changes due to a rapid correction, for example.

Accordingly, a specific fluctuation pattern in each of the driving information features due to the sleepiness is detected, and the sleepiness of the driver may thereby be detected (identified). More specifically, an arousal level identification model which may associate such a specific fluctuation pattern in each motion feature due to the sleepiness with the arousal level in such a case is generated, the generated arousal level identification model is used, and the sleepiness of the driver may thereby be identified.

In this embodiment, the first arousal level identification unit 122 uses the arousal level identification model that is generated in such a manner, thereby identifies the first arousal level from driving information features, and outputs the first arousal level as identification results to the arousal level estimation unit 15. Note that, as described above, the identification results include the arousal level that indicates any of level 1 to level 5 and the reliability that indicates the certainty of the arousal level in addition, for example. For example, as the identification results, arousal level: 3, reliability: 0.8, and so forth are output. Further, the generated arousal level identification model uses at least one or more driving information features, which are selected from the driving information features obtained from the driving information feature extraction unit 121, as input data and outputs the arousal level of the driver. The arousal level identification model may be generated by using a machine learning algorithm in related art such as a neural network, a support vector machine, or a random forest.

<Physiological Information Detection Unit 16>

The physiological information detection unit 16 detects one or more pieces of physiological information of the driver. In this embodiment, the physiological information detection unit 16 is configured with a sensor group for detecting the physiological information of the driver. For example, as illustrated in FIG. 4, the sensor group has an in-vehicle camera 161, a microphone 162, a heart rate sensor 163, a blood pressure sensor 164, and a body movement sensor 165. Note that the sensor group may further have a respiration sensor (not illustrated) that detects a respiration fluctuation of the driver, a skin temperature sensor (not illustrated) that detects the skin temperature of the driver, and so forth.

The in-vehicle camera 161 is arranged in the vehicle and images an internal portion of the vehicle. Then, the in-vehicle camera 161 generates image data that indicate a photographed image. For example, the in-vehicle camera 161 photographs the driver in driving. More specifically, the in-vehicle camera 161 is arranged to be capable of photographing the vicinity of a driver seat in the vehicle and photographs the driver on the driver seat.

The microphone 162 collects sound in the vehicle. More specifically, the microphone 162 is arranged in the vehicle to collect surrounding sound. Then, the microphone 162 generates data (audio data) that indicate the collected sound.

The heart rate sensor 163 detects a heart rate fluctuation of the driver. More specifically, the heart rate sensor 163 measures the heart rate of the driver and generates a sensor signal of the measurement result. Note that the heart rate sensor 163 may be a contact type sensor device that is attached to the body such as the earlobe or may be a contactless type sensor device such as a camera that extracts the change in the complexion which corresponds to a pulse wave. Further, the heart rate sensor 163 may be substituted by a pulse wave sensor and detect the heart rate fluctuation of the driver.

The blood pressure sensor 164 measures the blood pressure of the driver and generates a sensor signal of the measurement result. Here, the blood pressure sensor 164 is configured with a wearable device, for example, and is in advance attached to a person in charge who is to perform driving in the manual driving mode, that is, the driver.

The body movement sensor 165 detects the body movement such as the change in the posture of the driver. More specifically, the body movement sensor 165 is configured with a load sensor that is arranged in an internal portion of a backrest or a seating surface of the driver seat, for example. The body movement sensor 165 senses the change in the posture of a person on the driver seat and generates a sensor signal of the sensing result. Note that the body movement sensor 165 may be configured with an acceleration sensor, an angular velocity sensor, or the like.

<Second Arousal Level Recognition Unit 17>

The second arousal level recognition unit 17 recognizes second arousal level of the driver from one or more pieces of physiological information that are detected by the physiological information detection unit 16. Here, the physiological information may be information that indicates the heart rate fluctuation of the driver, may be a face image in which the face of the driver appears, or may be information that indicates the body movement of the driver, for example. Further, the physiological information may be information that indicates the respiration of the driver or may be information that indicates the blood pressure of the driver, for example. In this embodiment, as illustrated in FIG. 4, the second arousal level recognition unit 17 includes a physiological feature extraction unit 171 and a second arousal level identification unit 172. Note that in a case where the second arousal level recognition unit 17 receives the teacher data from a teacher data generation unit 152, which will be described later, the second arousal level recognition unit 17 performs learning for the second arousal level identification unit 172 based on the teacher data.

<<Physiological Feature Extraction Unit 171>>

The physiological feature extraction unit 171 extracts a physiological information feature related to the physiological state of the driver from each of plural pieces of physiological information that are detected by the physiological information detection unit 16.

Here, the physiological information feature is a feature for identifying the arousal level of the driver and a feature that is related to physiological information of the driver. The physiological information is an index that indicates a physiological state of a person such as sleepiness or fatigue and includes visual system physiological information, autonomic nervous system physiological information, skeletal system physiological information, or the like, for example. The visual system physiological information is a statistical feature such as the average value, standard deviation, or the like that is obtained from the fluctuation pattern in the eye opening ratio of the driver which indicates the opening degree of the eye of the driver, the frequency or time of eye blink of the driver, the position of the head of the driver, or the like in a prescribed unit time such as one minute, for example. Further, the autonomic nervous system physiological information is a statistical feature that is obtained from the fluctuation patterns in the respiration rate, the depth of respiration, the heart rate, the blood pressure, or the like in a prescribed unit time. Further, the skeletal system physiological information is a statistical feature that is obtained from the fluctuation pattern in the position of the center of gravity of the body in a prescribed unit time.

In this embodiment, the physiological feature extraction unit 171 includes one or more feature extraction units and extracts at least one or more features that indicate the physiological state of the driver. For example, as illustrated in FIG. 4, the physiological feature extraction unit 171 has a face image extraction unit 181, an eye opening ratio detection unit 182, an eye opening ratio feature extraction unit 183, an eye blink detection unit 184, an eye blink feature extraction unit 185, a head position detection unit 186, a head position feature extraction unit 187, a respiratory sound detection unit 188, a respiration feature extraction unit 189, a heart rate fluctuation detection unit 190, a heart rate fluctuation feature extraction unit 191, a blood pressure fluctuation detection unit 192, a blood pressure fluctuation feature extraction unit 193, a body movement detection unit 194, and a body movement feature extraction unit 195.

For example, the physiological feature extraction unit 171 uses the face image extraction unit 181 to the head position feature extraction unit 187 and may thereby extract an eye opening ratio feature, an eye blink feature, or a head position feature, which is related to the visual system physiological information of the driver, from an image which is photographed by the in-vehicle camera 161 and includes the driver, as the physiological information feature. Specifically, the face image extraction unit 181 consecutively acquires the image data from the in-vehicle camera 161 and extracts a face image region of the driver from the image data. The eye opening ratio detection unit 182 extracts the image region of the eye from the face image region extracted by the face image extraction unit 181, thereafter detects the upper and lower eyelids, and detects the eye opening ratio that indicates the opening degree of the eyelids, that is, the eye from the shapes of the eyelids. The eye opening ratio feature extraction unit 183 calculates an eye opening ratio feature, which is the average value, standard deviation, maximum value, minimum value, or the like of the eye opening ratio in a prescribed unit time, from the fluctuation pattern in the eye opening ratio that is detected by the eye opening ratio detection unit 182. Further, the eye blink detection unit 184 extracts the image region of the eye from the face image region extracted by the face image extraction unit 181, thereafter detects the upper and lower eyelids, and detects a blink (eye blink) from the movement of the upper and lower eyelids. The eye blink feature extraction unit 185 calculates an eye blink feature, which is the average value, standard deviation, or the like of the eye blink frequency or the eye blink time in a prescribed unit time. In addition, the head position detection unit 186 detects the fluctuation pattern in the head position of the driver based on the position in the image in the face image region extracted by the face image extraction unit 181. The head position feature extraction unit 187 calculates a head position feature, which is the average value, standard deviation, maximum value, minimum value, or the like of the head position in a prescribed unit time, from the fluctuation pattern in the head position.

Further, for example, the physiological feature extraction unit 171 uses the respiratory sound detection unit 188 and the respiration feature extraction unit 189 and may thereby extract a respiration feature, which is one of pieces of the autonomic nervous system physiological information of the driver, as the physiological information feature from collected sound data from the microphone 162 in the vehicle. Specifically, the respiratory sound detection unit 188 detects a respiratory sound pattern of the driver from the collected sound data from the microphone 162. The respiration feature extraction unit 189 calculates a respiration feature, which is the average value, standard deviation, maximum value, or the like of the respiration rate or the depth of respiration in a prescribed unit time, from the respiratory sound pattern that is detected by the respiratory sound detection unit 188.

Further, for example, the physiological feature extraction unit 171 uses the heart rate fluctuation detection unit 190 and the heart rate fluctuation feature extraction unit 191 and may thereby extract a heart rate fluctuation feature, which is one of pieces of the autonomic nervous system physiological information of the driver, as the physiological information feature from the heart rate sensor 163. Specifically, the heart rate fluctuation detection unit 190 detects an R wave that has the highest peak from an electrocardiographic waveform obtained from the heart rate sensor 163 and thereafter detects the fluctuation in a heartbeat interval that is the interval between the R waves (RR interval (RRI)) as a heart rate fluctuation pattern. The heart rate fluctuation feature extraction unit 191 calculates a heart rate fluctuation feature, which is the average value, standard deviation, or the like of the heartbeat interval (RRI) in a prescribed unit time, from the detected heart rate fluctuation pattern. Note that, as the heart rate fluctuation feature, after the frequency spectrum of the heart rate fluctuation pattern in a prescribed unit time is obtained, the ratio of power between a low frequency component (LF component) and a high frequency component (HF component) or the ratio between the LF component and the HF component (LF/HF ratio) may be used.

Further, for example, the physiological feature extraction unit 171 uses the blood pressure fluctuation detection unit 192 and the blood pressure fluctuation feature extraction unit 193 and may thereby extract a blood pressure fluctuation feature, which is one of the autonomic nervous system physiological information of the driver, as the physiological information feature from the blood pressure sensor 164. Specifically, the blood pressure fluctuation detection unit 192 detects a blood pressure fluctuation pattern of the driver from data obtained from the blood pressure sensor 164. The blood pressure fluctuation feature extraction unit 193 calculates a blood pressure fluctuation feature, which is the average value, standard deviation, maximum value, minimum value, or the like of the blood pressure in a prescribed unit time, from the detected blood pressure fluctuation pattern.

Further, for example, the physiological feature extraction unit 171 uses the body movement detection unit 194 and the body movement feature extraction unit 195 and may thereby extract a body movement feature, which is one of pieces of the skeletal system physiological information of the driver, as the physiological information feature from the body movement sensor 165. Specifically, the body movement detection unit 194 detects a body movement pattern that indicates the body movement of the driver from data obtained from the body movement sensor 165. The body movement feature extraction unit 195 calculates a body movement feature, which is the average value, standard deviation, maximum value, minimum value, or the like of the body movement frequency, the fluctuation amount of the position of the center of gravity of the body (body movement fluctuation amount), or the like in a prescribed unit time, from the detected body movement pattern.

<<Second Arousal Level Identification Unit 172>>

The second arousal level identification unit 172 identifies the second arousal level of the driver by using the physiological information features that are extracted by the physiological feature extraction unit 171.

In this embodiment, the second arousal level identification unit 172 identifies the arousal level of the driver by using at least one or more features that are obtained from one or more feature extraction units of the physiological feature extraction unit 171 and outputs identification results as the second arousal level. Note that the identification results include the arousal level that indicates any of level 1 to level 5 and the reliability of the arousal level, for example.

Here, a specific description will be made about an identification method of the second arousal level that is performed by the second arousal level identification unit 172.

It has been known that in a case where the arousal level of the driver lowers (the sleepiness becomes high) in driving, the visual system physiological information such as the eye opening ratio and the eye blink of the driver, the autonomic nervous system physiological information such as the heart rate and the pulse wave, and the skeletal system physiological information such as the body movement exhibit particular tendencies. First, a description will be made about the particular tendencies due to the sleepiness in relation to the visual system physiological information. Because the eyelids tend to close in a case where the sleepiness of the driver becomes high, a tendency is exhibited in which the eye opening ratio which indicates the opening degree of the eyelids becomes low. Further, a tendency is exhibited in which in a case where the sleepiness of the driver becomes high, the eye blink time of closing the eyelids for one eye blink becomes long, and the eye blink frequency in a prescribed unit time decreases. Further, because the head movement become unstable in a case where the sleepiness of the driver becomes high, a tendency is exhibited in which the head position unstably fluctuates.

Next, a description will be made about the particular tendencies due to the sleepiness in relation to the autonomic nervous system physiological information. Because one respiratory stroke becomes deep and the respiratory interval becomes long in a case where the sleepiness of the driver becomes high, a tendency is exhibited in which the respiration rate in a prescribed unit time decreases. Further, because the heart rate lowers in a case where the sleepiness of the driver becomes high, a tendency is exhibited in which the heartbeat interval (RRI) in a prescribed unit time becomes long. Further, as for the frequency spectrum of the heart rate fluctuation pattern (RRI), it has been known that the high frequency (HF: 0.15 to 0.4 Hz) component is low in an active condition and the HF component becomes high in a relaxed condition. Thus, the ratio between the low frequency (LF: 0.04 to 0.15 Hz) component and the HF component (LF/HF) is often used as an index of sleepiness. That is, a tendency is exhibited in which the LF/HF ratio of the driver becomes low in a case where the sleepiness of the driver becomes high. Further, a tendency is exhibited in which the blood pressure temporarily rises because the driver resists the sleepiness in a case where the driver starts feeling the sleepiness but the blood pressure gradually falls in a case where the sleepiness of the driver further becomes high.

Finally, a description will be made about the particular tendencies due to the sleepiness in relation to the skeletal system physiological information. A tendency is exhibited in which the body movement frequency increases in order to resist the sleepiness and the body movement fluctuation amount also increases in a case where the driver starts feeling the sleepiness. Further, a tendency is exhibited in which in a case where the sleepiness of the driver further becomes high, the driver may not resist the sleepiness, and the body movement frequency and the body movement fluctuation amount decrease.

In such a manner, each of the physiological information features due to the sleepiness exhibits a particular tendency, that is, a specific fluctuation pattern. Accordingly, the specific fluctuation pattern in each of the physiological information features due to the sleepiness is detected, and the sleepiness of the driver may thereby be detected (identified). More specifically, an arousal level identification model which may associate such a specific fluctuation pattern in each of the physiological information features due to the sleepiness with the arousal level in such a case is generated, the generated arousal level identification model is used, and the sleepiness of the driver may thereby be identified.

In this embodiment, the second arousal level identification unit 172 uses the arousal level identification model that is generated in such a manner, thereby identifies the second arousal level from physiological information features, and outputs the second arousal level as identification results to the arousal level estimation unit 15. Note that, as described above, the identification results include the arousal level that indicates any of level 1 to level 5 and the reliability that indicates the certainty of the arousal level in addition, for example. For example, as the identification results, arousal level: 3, reliability: 0.8, and so forth are output. Further, the generated arousal level identification model uses at least one or more physiological information features, which are selected from the physiological information features obtained from the physiological feature extraction unit 171, as input data and outputs the arousal level of the driver. The arousal level identification model may be generated by using the machine learning algorithm in related art such as the neural network, the support vector machine, or the random forest.

Note that the second arousal level identification unit 172 performs learning based on the teacher data generated by the teacher data generation unit 152, which will be described later. More specifically, in the second arousal level identification unit 172, in a case where the first arousal level is different from the second arousal level in the manual driving mode, a learning process is performed by using the teacher data that are generated by the teacher data generation unit 152 based on the first arousal level. That is, in the learning, model update is performed such that the arousal level identification model of the second arousal level identification unit 172, which indicates the relationship between one or more pieces of physiological information of the driver and the arousal level of the driver, outputs the first arousal level as the identification result from the teacher data.

In this embodiment, in a case where the second arousal level identification unit 172 acquires the teacher data from the teacher data generation unit 152, the second arousal level identification unit 172 performs learning for the arousal level identification model that is used for identifying the second arousal level by using the teacher data. Note that, as a specific learning method, for example, a backpropagation method or the like may be used in a case where the arousal level identification model is a hierarchical neural network.

<Arousal Level Estimation Unit 15>

The arousal level estimation unit 15 estimates third arousal level of the driver in driving of the vehicle from at least one of the first arousal level that is recognized by the first arousal level recognition unit 12 and the second arousal level that is recognized by the second arousal level recognition unit 17.

Here, the arousal level estimation unit 15 may estimate the third arousal level from the first arousal level and the second arousal level in the manual driving mode and estimate the third arousal level from the second arousal level in the automated driving mode. More specifically, the arousal level estimation unit 15 may set the second arousal level as the third arousal level and thereby estimate the third arousal level from the second arousal level in the automated driving mode. Further, in the manual driving mode, the arousal level estimation unit 15 may assess whether or not the reliability of each of the first arousal level and the second arousal level is a threshold value or higher, set either one of the first arousal level and the second arousal level, whose reliability is the threshold value or higher, as the third arousal level, and thereby estimate the third arousal level. More specifically, in the manual driving mode, in a case where the reliability of each of the first arousal level and the second arousal level is the threshold value or higher and the first arousal level is different from the second arousal level, the arousal level estimation unit 15 may set the first arousal level as the third arousal level and thereby estimate the third arousal level.

Note that in a case where the first arousal level is different from the second arousal level in the manual driving mode, the arousal level estimation unit 15 performs a learning process by using the teacher data that are generated based on the first arousal level.

In this embodiment, as illustrated in FIG. 1, the arousal level estimation unit 15 includes an arousal level verification unit 151 and the teacher data generation unit 152. The arousal level estimation unit 15 estimates the third arousal level as final arousal level of the driver based on the first arousal level that is obtained from the first arousal level recognition unit 12 or the second arousal level that is obtained from the second arousal level recognition unit 17.

<<Arousal Level Verification Unit 151>>

The arousal level verification unit 151 verifies the validity of the first arousal level that is obtained from the first arousal level recognition unit 12 or the validity of the second arousal level that is obtained from the second arousal level recognition unit 17. Here, as for a verification method of the validity of the first arousal level, in a case where the reliability of the arousal level included in the identification results obtained from the first arousal level identification unit 122 is a predetermined threshold value or higher, the first arousal level may be assessed as valid. Further, as for a verification method of the validity of the second arousal level, the same method as the above-described first arousal level may be used.

The arousal level verification unit 151 outputs either one of the first arousal level and the second arousal level as the final arousal level of the driver, that is, the third arousal level based on the verification results and the driving mode selected by the driving mode selection unit 6. For example, in a case where the driving mode is the manual driving mode, the arousal level verification unit 151 may output the first arousal level as the third arousal level after confirmation of the validity of the first arousal level. Further, for example, in a case where the driving mode is the automated driving mode, the arousal level verification unit 151 may output the second arousal level as the third arousal level after confirmation of the validity of the second arousal level.

Further, in a case where the driving mode is the manual driving mode, the arousal level verification unit 151 performs a comparison about whether the value of the first arousal level is different from the value of the second arousal level. In a case where those are different, a learning trigger signal is output to the teacher data generation unit 152.

<<Teacher Data Generation Unit 152>>

The teacher data generation unit 152 generates the teacher data from the first arousal level in the manual driving mode, outputs the teacher data to the second arousal level recognition unit 17, thereby causes the second arousal level identification unit 172 to perform the learning process. More specifically, in a case where the teacher data generation unit 152 receives the learning trigger signal from the arousal level verification unit 151, the teacher data generation unit 152 generates the teacher data by using the first arousal level and outputs the teacher data to the second arousal level identification unit 172. Note that the teacher data generation unit 152 generates the teacher data such that the teacher data conform to the arousal level identification model that is used by the second arousal level identification unit 172.

Consequently, the teacher data generation unit 152 may cause the second arousal level identification unit 172 to perform the learning process by using the teacher data that are generated based on the first arousal level. Note that, as described above, the learning process is performed by the second arousal level recognition unit 17 based on the teacher data in a case where the second arousal level recognition unit 17 acquires (receives) the teacher data from the teacher data generation unit 152.

[Action of Arousal Level Estimation Device 10]

Next, a description will be made about an action of the arousal level estimation device 10 that is configured as described earlier.

Figure 5:
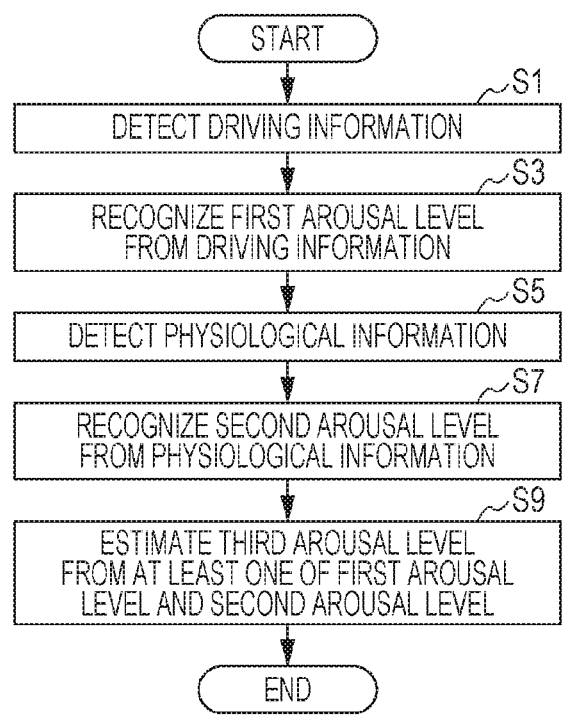
FIG. 5 is a flowchart that illustrates an outline of a process that is performed by an arousal level estimation device in the embodiment.

FIG. 5 is a flowchart that illustrates an outline of a process that is performed by the arousal level estimation device 10 in this embodiment.

As illustrated in FIG. 5, the arousal level estimation device 10 first detects the driving information (S1). Note that the details are described above and will thus not be described here. Next, the arousal level estimation device 10 recognizes the first arousal level of the driver from the driving information that is detected in S1 (S3). Next, the arousal level estimation device 10 detects the physiological information of the driver (S5). Next, the arousal level estimation device 10 recognizes the second arousal level of the driver from the physiological information that is detected in S5 (S7). Finally, the arousal level estimation device 10 estimates the third arousal level of the driver in driving of the vehicle from at least one of the first arousal level that is recognized in S3 and the second arousal level that is recognized in S7 (S9). In S9, as described above, the arousal level estimation device 10 estimates the third arousal level from the first arousal level and the second arousal level in the manual driving mode and estimates the third arousal level from the second arousal level in the automated driving mode.

Note that a process of S5 may be performed after a process of S1 or a process of S3 but may be performed simultaneously with the process of S1 or the process of S3 or may be performed in parallel with the process of S1. Further, a process of S7 may be performed in parallel with the process of S3 in a case where the process of S7 is performed after the process of S5.

[Action of Driving Support Device 1]

Figure 6A:
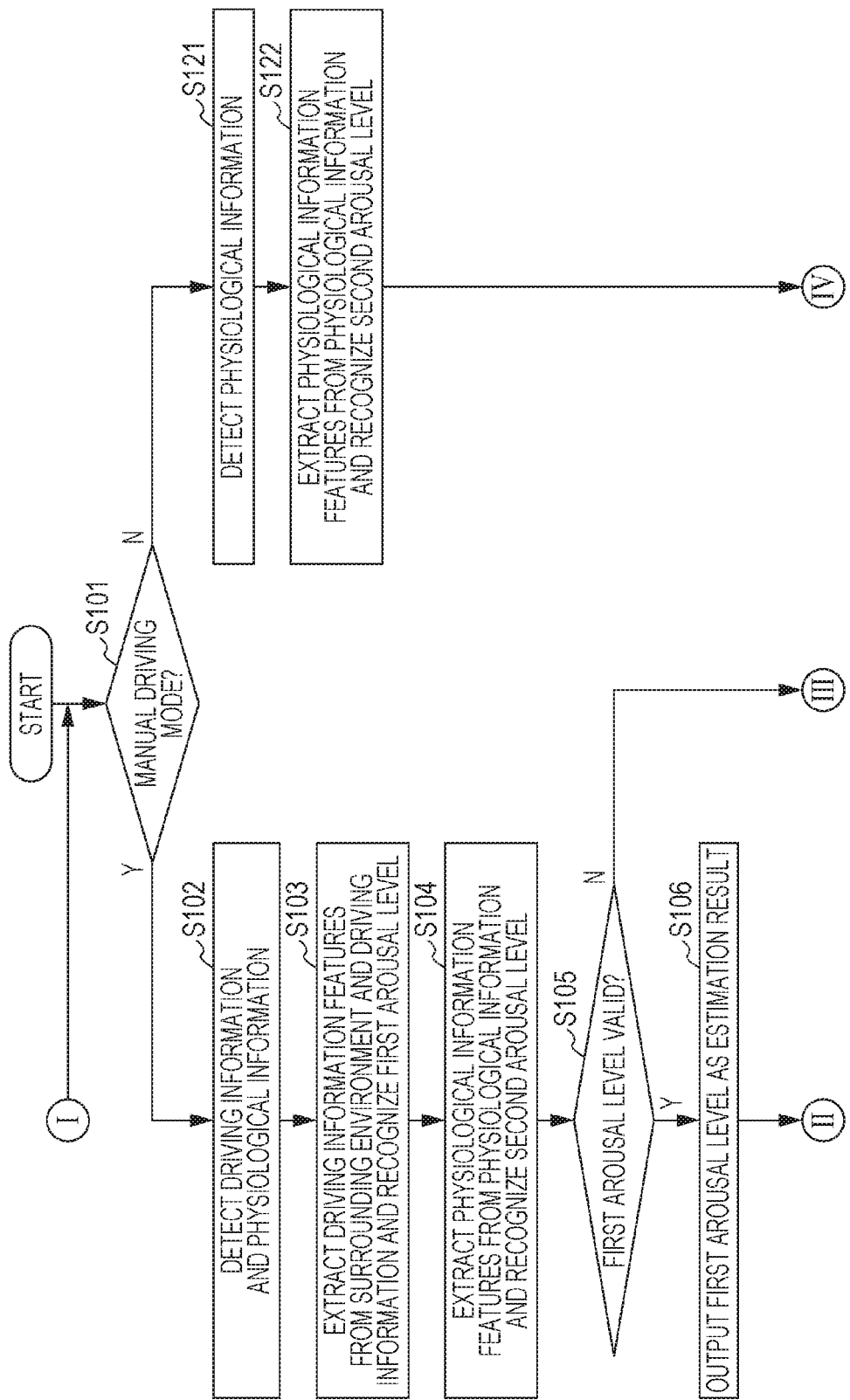
FIGS. 6A and 6B are flowcharts that illustrate an action that is performed by the arousal level estimation device in the embodiment.
Figure 6B:
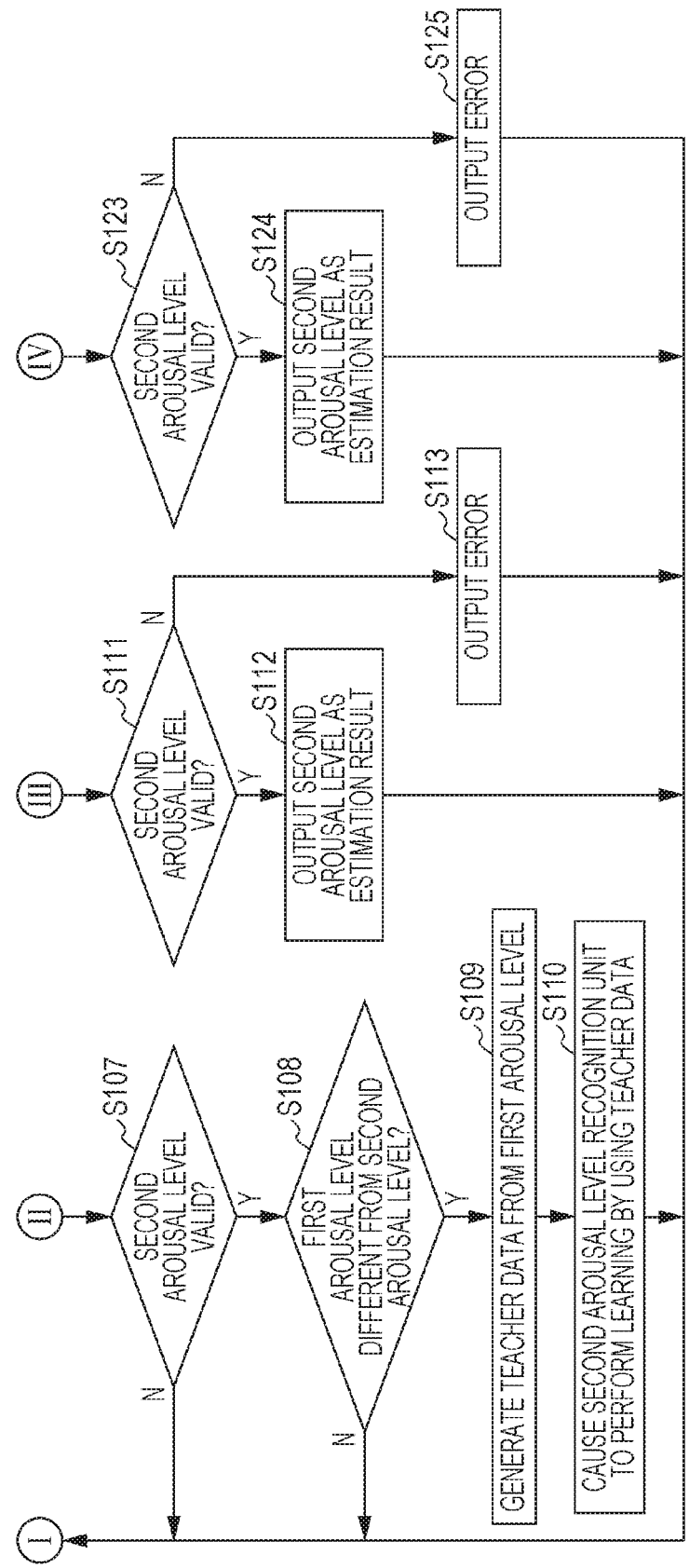

FIGS. 6A and 6B are flowcharts that illustrate an action that is performed by the driving support device 1 in this embodiment. Note that, as described above, the driving support device 1 is capable of switching the automated driving mode in which the travel control of the vehicle is automatically performed and the manual driving mode by the driver, in the driving mode selection unit 6. Further, regardless of the driving mode, the driving support device 1 regularly monitors the information related to the surrounding environment around the traveling vehicle such as the vehicular gap from the preceding vehicle by the surrounding environment recognition unit 3 or the subject vehicle position detection unit 4.

Referring to FIGS. 6A and 6B, a description will first be made about an action that is performed by the driving support device 1 in the manual driving mode while the action of the arousal level estimation device 10 is focused.

It is assumed that in S101, the arousal level estimation device 10 assesses whether or not the driving mode is the manual driving mode and assesses the driving mode as the manual driving mode (Y in S101). More specifically, in a case where the manual driving mode is selected by the driving mode selection unit 6, the arousal level estimation unit 15 assesses the driving mode as the manual driving mode. In this case, the driver performs driving of the vehicle, that is, the travel control of the vehicle by using the driving operation unit 2.

Next, the arousal level estimation device 10 detects the driving information and the physiological information of the driver (S102). Specifically, while the driver is performing driving in the manual driving mode, the vehicle behavior detection unit 11 detects the driving information of the driving operation by the driver, and the physiological information detection unit 16 detects the physiological information of the driver.

Next, the arousal level estimation device 10 extracts the driving information features from the surrounding environment and the driving information and thereby recognizes the first arousal level (S103). Specifically, the first arousal level recognition unit 12 recognizes the first arousal level of the driver by using the surrounding environment of the subject vehicle that is obtained from the surrounding environment recognition unit 3 and the driving information that is obtained from the vehicle behavior detection unit 11. More specifically, as described above, the driving information feature extraction unit 121 extracts the driving information features based on the surrounding environment of the subject vehicle and the driving information, and the first arousal level identification unit 122 identifies the first arousal level by using the driving information features that are extracted by the driving information feature extraction unit 121.

Next, the arousal level estimation device 10 extracts the physiological information features from the physiological information and thereby recognizes the second arousal level (S104). Specifically, the second arousal level recognition unit 17 recognizes the second arousal level by using the physiological information that is obtained from the physiological information detection unit 16. More specifically, as described above, the physiological feature extraction unit 171 extracts the physiological information features based on the physiological information, and the second arousal level identification unit 172 identifies the second arousal level by using the physiological information features that are extracted by the physiological feature extraction unit 171.

Next, the arousal level estimation unit 15 estimates the third arousal level as the final arousal level of the driver based on the first arousal level and the second arousal level (S105 and S106). Specifically, first, the arousal level verification unit 151 of the arousal level estimation unit 15 verifies the validity of the first arousal level that is recognized in S103 (S105). Note that, as for the verification method of the validity of the first arousal level, in a case where the reliability of the arousal level included in the identification results obtained from the first arousal level identification unit 122 is a predetermined threshold value or higher, the first arousal level may be assessed as valid. In S105, in a case where the first arousal level is assessed as valid (Y in S105), the first arousal level is output as the estimation result, that is, the third arousal level (S106).

Next, the arousal level verification unit 151 verifies the validity of the second arousal level that is recognized in S104 (S107). Note that, as for the verification method of the validity of the second arousal level, the same method as the above-described first arousal level may be used.

In S107, in a case where the second arousal level is assessed as valid (Y in S107), the comparison is performed between the first arousal level and the second arousal level, and an assessment whether or not those are different is performed (S108).

In S108, in a case where the first arousal level is different from the second arousal level (Y in S108), the arousal level verification unit 151 outputs the result to the teacher data generation unit 152. In this embodiment, in a case where the first arousal level is different from the second arousal level as a result of the comparison, the arousal level verification unit 151 outputs the learning trigger signal to the teacher data generation unit 152.

Next, the teacher data generation unit 152 generates the teacher data from the first arousal level (S109) and outputs the generated teacher data to the second arousal level recognition unit 17. In this embodiment, in a case where the teacher data generation unit 152 receives the learning trigger signal from the arousal level verification unit 151, the teacher data generation unit 152 generates the teacher data by using the first arousal level and outputs the teacher data to the second arousal level identification unit 172. Note that the teacher data generation unit 152 generates the teacher data such that the teacher data conform to the arousal level identification model that is used by the second arousal level identification unit 172.

Next, the second arousal level recognition unit 17 performs the learning process based on the teacher data that are obtained from the teacher data generation unit 152 (S110). Then, the action returns to a process of S101, and the processes are repeated. In this embodiment, in a case where the second arousal level identification unit 172 acquires the teacher data from the teacher data generation unit 152, the second arousal level identification unit 172 performs learning for the arousal level identification model that is used for identifying the second arousal level by using the teacher data. The action thereafter returns to the process of S101.

Note that in a case where the second arousal level is not valid in S107 (N in S107) or in a case where the first arousal level matches the second arousal level in S108 (N in S108), the learning process by the second arousal level recognition unit 17 is not performed, the action returns to the process of S101, and the processes are repeated.

Further, in S105, in a case where the first arousal level recognized in S103 is not assessed as valid (N in S105), the arousal level verification unit 151 verifies the validity of the second arousal level recognized in S104 (S111). In S111, in a case where the second arousal level recognized in S104 is assessed as valid (Y in S111), the arousal level verification unit 151 outputs the second arousal level recognized in S104 as the estimation result, that is, the third arousal level (S112). On the other hand, in S111, in a case where the second arousal level recognized in S104 is not valid (N in S111), the arousal level verification unit 151 outputs an error that indicates that the third arousal level may not be estimated (S113), and the action returns to the process of S101.

Referring to FIGS. 6A and 6B, a description will next be made about an action that is performed by the driving support device 1 in the automated driving mode while the action of the arousal level estimation device 10 is focused.

It is assumed that in S101, the arousal level estimation device 10 assesses whether or not the driving mode is the manual driving mode and assesses the driving mode as not the manual driving mode (N in S101). More specifically, in a case where the automated driving mode is selected by the driving mode selection unit 6, the arousal level estimation unit 15 assesses the driving mode as the automated driving mode. In this case, the driver does not have to perform the driving operation, and the vehicle control unit 7 automatically performs automated driving, that is, the travel control of the vehicle based on the surrounding environment.

Next, the arousal level estimation device 10 detects the physiological information of the driver (S121). Specifically, in the automated driving mode, the physiological information detection unit 16 detects the physiological information of the driver. Here, in the automated driving mode, because the driver himself/herself does not perform the driving operation, the vehicle behavior detection unit 11 may not obtain effective driving information based on the driving operation by the driver such as the steering angle in steering. On the other hand, the physiological information detection unit 16 may obtain effective physiological information of the driver even in the automated driving.

Next, the arousal level estimation device 10 extracts the physiological information features from the physiological information and thereby recognizes the second arousal level (S122). Specifically, the second arousal level recognition unit 17 recognizes the second arousal level by using the physiological information that is obtained from the physiological information detection unit 16. More specifically, as described above, the physiological feature extraction unit 171 extracts the physiological information features based on the physiological information, and the second arousal level identification unit 172 identifies the second arousal level by using the physiological information features that are extracted by the physiological feature extraction unit 171. In such a manner, the arousal level estimation device 10 recognizes the arousal level of the driver from the physiological information of the driver not by using the first arousal level recognition unit 12 but by using the second arousal level recognition unit 17.

Next, the arousal level estimation unit 15 estimates the third arousal level as the final arousal level of the driver based on the second arousal level (S123 and S124). Specifically, first, the arousal level verification unit 151 of the arousal level estimation unit 15 verifies the validity of the second arousal level that is recognized in S122 (S123). Note that, as for the verification method of the validity of the second arousal level, the same method as the above-described first arousal level may be used. In S123, in a case where the second arousal level is assessed as valid (Y in S123), the second arousal level is output as the estimation result, that is, the third arousal level (S124). Note that in a case where the second arousal level is not valid in S123 (N in S123), the arousal level verification unit 151 outputs the error that indicates that the third arousal level may not be estimated (S125), and the action returns to the process of S101.

[Effects]

As described earlier, this embodiment may realize an arousal level estimation device that may highly precisely estimate the arousal level of the driver of the vehicle that has the automated driving mode and the manual driving mode.

More specifically, the arousal level estimation device 10 in this embodiment estimates the final estimation result, that is, the third arousal level by using the first arousal level that is recognized by using the driving information of the driver and the second arousal level that is recognized by using the physiological information of the driver in the manual driving mode. Meanwhile, the arousal level estimation device 10 sets the second arousal level, which is recognized by using the physiological information of the driver, as the final estimation result, that is, the third arousal level in the automated driving mode. That is, in the arousal level estimation device 10 in this embodiment, in the manual driving mode and the automated driving mode, the third arousal level of the driver is estimated by using the first arousal level recognized by the first arousal level recognition unit 12 and the second arousal level recognized by the second arousal level recognition unit 17 while switching is appropriately made between the first arousal level and the second arousal level.

In addition, in the manual driving mode, the arousal level estimation device 10 in this embodiment causes the second arousal level recognition unit 17 to perform the learning process by using recognition results of the first arousal level recognition unit 12 as the teacher data. Consequently, variations in the precision of recognition of the second arousal level due to individual differences in the physiological information may be absorbed. Consequently, in the automated driving mode, the arousal level estimation device 10 in this embodiment may precisely estimate the arousal level of the driver based on the physiological information of the driver. That is, it is possible to precisely estimate the arousal level of the driver even in the automated driving at level 2 or higher in which the driving information such as the driving operation by the driver or vehicle behavior may not be used.

As described in the foregoing, because the arousal level estimation device 10 in this embodiment may precisely estimate the arousal level of the driver based on the physiological information of the driver, the arousal level of the driver may precisely be detected even in an automated driving system that includes the automated driving mode at level 2 or higher.

Modification Example

In the above embodiment, the method is described in which the teacher data generated by the teacher data generation unit 152 are used and the arousal level identification model itself that is used by the second arousal level identification unit 172 is thereby learned. However, embodiments are not limited to this. The learning process may be performed by using the first arousal level as the teacher data and by selecting the physiological information features that are effective for identification of the second arousal level from plural physiological information features obtained from the physiological feature extraction unit 171. This case will be described as a modification example in the following.

FIG. 7 is a block diagram that illustrates one example of a configuration of the driving support device in the modification example. Note that the same wording is used for similar contents to FIG. 1, and a detailed description will not be made. In the driving support device 1 in the modification example illustrated in FIG. 7, the configuration of a second arousal level recognition unit 17A of an arousal level estimation device 10A is different from the driving support device 1 in the above embodiment. Specifically, in the arousal level estimation device 10A in the modification example, a physiological information feature storage unit 173 and a physiological feature selection unit 174 are added to the second arousal level recognition unit 17 in the above embodiment, and the configurations of a physiological feature extraction unit 171A and a second arousal level identification unit 172A are different.

<Physiological Feature Extraction Unit 171A>

The physiological feature extraction unit 171A extracts the physiological information feature from each of plural pieces of physiological information that are detected by the physiological information detection unit 16. The physiological feature extraction unit 171A outputs the extracted physiological information features to the physiological feature selection unit 174. Note that in the automated driving mode, the physiological feature extraction unit 171A may output the extracted physiological information features to the second arousal level identification unit 172A.

<Physiological Information Feature Storage Unit 173>

The physiological information feature storage unit 173 stores the physiological information features that are obtained from the physiological feature extraction unit 171A. The physiological information feature storage unit 173 may store the teacher data that are obtained from the teacher data generation unit 152.

<Physiological Feature Selection Unit 174>

In the manual driving mode, the physiological feature selection unit 174 selects the physiological information features, which are highly correlated with the teacher data generated from the first arousal level by the teacher data generation unit 152, among the plural physiological information features extracted by the physiological feature extraction unit 171A.

More specifically, in the manual driving mode, the physiological feature selection unit 174 stores teacher data D(t) (t represents the time) that are obtained from the teacher data generation unit 152 in a prescribed storage unit for predetermined times (m times) as teacher data series D(1), D(2), ..., D(m). In this modification example, a description will be made in the following on an assumption that the teacher data D(t) are stored in the physiological information feature storage unit 173. Further, in the manual driving mode, the physiological feature selection unit 174 stores n kinds of physiological information features Bi(t) (i=1 to n) that are obtained from the physiological feature extraction unit 171A in the physiological information feature storage unit 173 for predetermined times (m times) as physiological information feature data series Bi(1), Bi(2), ..., Bi(m).

In the manual driving mode, for example, in a case where a predetermined number of data series are stored in the physiological information feature storage unit 173, the physiological feature selection unit 174 calculates the correlation coefficient between the teacher data series D(t) (t=1, 2, ..., m) stored in the physiological information feature storage unit 173 and the n kinds of physiological information feature data series Bi(t) (t=1, 2, ..., m) stored in the physiological information feature storage unit 173. Note that the correlation coefficient may be calculated by a method in related art such as calculation by dividing the covariance between D(t) and Bi(t) by the product value of the standard deviation of D(t) and the standard deviation of Bi(t), for example.

In the manual driving mode, the physiological feature selection unit 174 compares the calculated correlation coefficient with a predetermined threshold value, selects the physiological information features whose correlation coefficient is the threshold value or higher, and outputs the physiological information features to the second arousal level identification unit 172A. Note that in the automated driving mode, the physiological feature selection unit 174 may output the physiological information features that are selected in the manual driving mode to the second arousal level identification unit 172A.

<Second Arousal Level Identification Unit 172A>

In the automated driving mode and the manual driving mode, the second arousal level identification unit 172A identifies the second arousal level by using the physiological information features that are selected by the physiological feature selection unit 174.

In the manual driving mode, the second arousal level identification unit 172A performs the learning process based on the teacher data generated by the teacher data generation unit 152. In this modification example, in a case where the second arousal level recognition unit 17A receives the teacher data from the teacher data generation unit 152, the second arousal level identification unit 172A performs the learning process by using the physiological information features that are selected by the physiological feature selection unit 174 as the teacher data. Note that in a case where the kinds of physiological information features, which are the physiological information features selected by the physiological feature selection unit 174 and are used for identification of the second arousal level, are changed, the second arousal level identification unit 172A has to generate (learn) the arousal level identification model by using only the selected physiological information features.

[Effects]

As described earlier, this modification example may realize an arousal level estimation device that may highly precisely estimate the arousal level of the driver of the vehicle that has the automated driving mode and the manual driving mode.

More specifically, in the arousal level estimation device 10A in this modification example, in the manual driving mode, the physiological feature selection unit 174 selects the physiological information features, which are highly correlated with the first arousal level as the teacher data, among the plural kinds of physiological information features that are obtained from the physiological feature extraction unit 171A. Further, the second arousal level may be identified by using the arousal level identification model that performs the learning process with the selected physiological information features as the teacher data.

In such a manner, the arousal level estimation device 10A in this modification example may generate (learn) the arousal level identification model while selecting physiological information features that are effective for identification of the arousal level and may thus absorb variations due to individual differences in the physiological information.

In addition, in this modification example, the second arousal level identification unit 172A may reduce the processing amount compared to a case where the second arousal level is identified by using all the physiological information features that are obtained from the physiological feature extraction unit 171A and may thus increase the processing speed of the second arousal level identification unit 172A.

Other Embodiments

The present disclosure is not limited to the above embodiment. For example, other embodiments that are realized by arbitrarily combining the configuration elements described herein or omitting several configuration elements may be provided as embodiments of the present disclosure. Further, the present disclosure includes modification examples that are obtained by applying various modifications conceived by persons having ordinary skill in the art within the scope which does not depart from the gist of the present disclosure in relation to the above embodiment, that is, the meanings indicated by the wording described in the claims.

For example, in the above-described driving support device 1, each configuration element in each of the units such as the surrounding environment recognition unit 3, the subject vehicle position detection unit 4, the target travel state decision unit 5, the driving mode selection unit 6, the vehicle control unit 7, the notification unit 8, and the vehicle behavior detection unit 11, the first arousal level recognition unit 12, the physiological information detection unit 16, the second arousal level recognition unit 17, and the arousal level estimation unit 15, which are included in the arousal level estimation device 10, may be configured with dedicated hardware. Further, the configuration element may be realized by executing a software program that is suitable for each of the configuration elements. Further, a program execution unit such as a CPU or a processor reads out and executes a software program that is recorded in a recording medium such as a hard disk or a semiconductor memory, and each of the configuration elements may thereby be realized.

Further, the present disclosure also includes cases described in the following.

(1) The above devices are computer systems that are specifically configured with a microprocessor, a ROM, a RAM, a hard disk unit, a display unit, a keyboard, a mouse, and so forth. The RAM or the hard disk unit stores a computer program. The microprocessor acts in accordance with the computer program, and the devices thereby achieve their functions. Here, the computer program is configured by combining plural instruction codes that indicate commands for a computer in order to achieve a prescribed function.

(2) In addition, a portion of or all configuration elements that configure the above devices may be configured with one system large scale integration (LSI). A system LSI is a super multi-function LSI that is manufactured by integrating plural configuration units on one chip and is specifically a computer system configured to include a microprocessor, a ROM, a RAM, and so forth. The RAM stores a computer program. The microprocessor acts in accordance with the computer program, and the system LSI thereby achieves its function.

(3) A portion of or all configuration elements that configure the above devices may be configured with IC cards or individual modules that are removable from the devices. The IC card or the module is a computer system that is configured with a microprocessor, a ROM, a RAM, and so forth. The IC card or the module may include the above super multi-function LSI. The microprocessor acts in accordance with a computer program, and the IC card or the module thereby achieves its function. The IC card or the module may be tamper-resistant.

(4) Further, one embodiment of the present disclosure may be the methods that are described above. Further, one embodiment of the present disclosure may be a computer program that realizes those methods by a computer or digital signals that are configured with the computer program.

(5) Further, one embodiment of the present disclosure may be the computer program or the digital signals that are recorded in computer-readable recording media such as a flexible disk, a hard disk, a CD-ROM, an MO, a DVD, a DVD-ROM, a DVD-RAM, a Blu-ray® disc (BD), or a semiconductor memory, for example. Further, one embodiment of the present disclosure may be the digital signals that are recorded in those recording media.

(6) Further, one embodiment of the present disclosure may be the computer program or the digital signals that are transmitted via an electric communication line, a wireless or wired communication line, a network represented by the Internet, data broadcasting, and so forth.

(7) Further, one embodiment of the present disclosure may be a computer system that includes a microprocessor and a memory, in which the memory stores the computer program and the microprocessor acts in accordance with the computer program.

(8) Further, one embodiment of the present disclosure may be practiced by another independent computer system by transferring the recording media that record the program or the digital signals or by transferring the program or the digital signals via the network or the like.

(9) Further, all the numerals used in the above are exemplified for specifically describing the present disclosure, and the present disclosure is not restricted by the exemplified numerals.

(10) Further, the divisions of the function blocks in the block diagrams are examples. Plural function blocks may be realized as one function block, one function block may be divided into plural function blocks, or a portion of functions may be moved to another function block. Further, the functions of plural function blocks that have similar functions may be processed by a single piece of hardware or software in parallel or in a time-division manner.

(11) Further, the order of execution of plural steps included in the above arousal level estimation method is for exemplification for specifically describing the present disclosure and may be another order than the above. Further, a portion of the above steps may simultaneously (in parallel) be executed with the other steps.

<<Supplement>>

Each of the various arousal level estimation devices that are described in the above embodiments and modification example is one example of "system for assessing arousal level of a driver of a vehicle" according to the present disclosure. Each of the arousal level estimation methods that are described in the above embodiments and modification example is one example of "method for assessing arousal level of a driver of a vehicle" according to the present disclosure.

The arousal level assessment device according to one aspect of the present disclosure may not include sensors such as the vehicle behavior detection unit and the physiological information detection unit and may receive the driving information and the physiological information from sensors that are provided on the outside of the arousal level assessment device, for example. In this case, the arousal level assessment device includes a memory that records programs and a processor, for example, and the processor executes assessment of the arousal level of the driver in accordance with the programs read out from the memory. In addition, the arousal level assessment device according to one aspect of the present disclosure may receive driving features extracted from the driving information and/or physiological features extracted from the physiological information from outside sensors, for example.

"First mode" according to one aspect of the present disclosure may be a mode in which control in both of the front-rear direction and the left-right direction of the vehicle is performed by the driver, for example. "Second mode" may be a mode in which control of at least one of the front-rear direction and the left-right direction of the vehicle is performed automatically, for example.

An arousal level assessment system and an arousal level assessment method according to one aspect of the present disclosure may be installed in a driving support system or the like that estimates arousal level of a driver in driving and alerts the driver in a case where the arousal level becomes lower than a prescribed value.

What is claimed is:

1. An apparatus for assessing an arousal level of a driver of a vehicle, the apparatus comprising:
   a processor; and
   a memory storing a computer program, which when executed by the processor, causes the processor to perform operations including, acquiring personal data of the driver, which are detected by one or more sensors when the vehicle is traveling, developing, by machine learning with the acquired personal data, a model for estimating an arousal level to personalize the model to the driver, and determining the arousal level of the driver based on the personalized model, wherein the determining is performed when at least part of the travel control is automatically performed by an automatic driving mode.

2. The apparatus according to claim 1,
wherein the personal data are detected during a period after the vehicle starts traveling.

3. The apparatus according to claim 1,
wherein the personal data are detected at a timing until the vehicle starts autonomous travelling after the vehicle starts traveling.

4. The apparatus according to claim 1,
wherein the personal data are detected when travel control of the vehicle is performed by the driver.

5. The apparatus according to claim 1,
wherein the personal data include physiological information related to a physiological state of the driver, and the model indicates a relationship between the physiological state and the arousal level.

6. The apparatus according to claim 1,
wherein the model is, in an initial state, a general model for a plurality of drivers.

7. The apparatus according to claim 1,
wherein the personal data include
driving information related to a driving operation by the driver and/or a travelling state of the vehicle, and
physiological information related to a physiological state of the driver.

8. The apparatus according to claim 1,
wherein, in the determining, the arousal level of the driver is determined by using the physiological information without referring to the driving information.

9. The apparatus according to claim 1,
wherein the one or more sensor includes a camera that captures an image of a face of the driver.

10. A vehicle, comprising:
a controller that performs travel control of the vehicle in either a first mode or a second mode; and
the apparatus according to claim 1.

* * * * *